(12) United States Patent
Zarreii

(10) Patent No.: US 11,559,243 B2
(45) Date of Patent: *Jan. 24, 2023

(54) SYSTEM AND METHOD FOR EVALUATING NEUROLOGICAL CONDITIONS

(71) Applicant: Mansour Zarreii, Mechanicsburg, PA (US)

(72) Inventor: Mansour Zarreii, Mechanicsburg, PA (US)

( * ) Notice: Subject to any disclaimer, the term of this patent is extended or adjusted under 35 U.S.C. 154(b) by 187 days.

This patent is subject to a terminal disclaimer.

(21) Appl. No.: 16/936,511

(22) Filed: Jul. 23, 2020

(65) Prior Publication Data

US 2020/0352469 A1    Nov. 12, 2020

Related U.S. Application Data

(63) Continuation of application No. 15/885,960, filed on Feb. 1, 2018, now Pat. No. 10,736,534, which is a continuation of application No. 15/588,219, filed on May 5, 2017, now Pat. No. 9,883,814.

(51) Int. Cl.
| | |
|---|---|
| *A61B 3/14* | (2006.01) |
| *A61B 5/377* | (2021.01) |
| *G06F 16/9535* | (2019.01) |
| *G06Q 30/06* | (2012.01) |
| *G06Q 20/08* | (2012.01) |
| *A61B 5/00* | (2006.01) |

(52) U.S. Cl.
CPC ............ *A61B 5/377* (2021.01); *A61B 5/4076* (2013.01); *A61B 5/6814* (2013.01); *A61B 5/7225* (2013.01); *G06F 16/9535* (2019.01); *G06Q 20/085* (2013.01); *G06Q 30/0619* (2013.01); *G06Q 30/0621* (2013.01); *G06Q 30/0643* (2013.01); *A61B 2562/164* (2013.01)

(58) Field of Classification Search
CPC ....... A61B 3/032; A61B 3/024; A61B 3/0091; A61B 3/113; A61B 3/14; A61B 5/6803; A61B 5/16; A61B 5/163; A61B 5/6821
USPC ......... 351/209, 210, 224, 237, 246; 600/558
See application file for complete search history.

(56) References Cited

U.S. PATENT DOCUMENTS

| | | | |
|---|---|---|---|
| 3,462,604 | A | 8/1969 | Mason |
| 3,902,795 | A | 9/1975 | Owen |
| 4,735,498 | A | 4/1988 | Udden et al. |
| 4,836,670 | A | 6/1989 | Hutchinson |
| 4,973,149 | A | 11/1990 | Hutchinson |
| 5,343,261 | A | 8/1994 | Wilson |
| 5,661,538 | A | 8/1997 | Carter |
| 6,102,870 | A | 8/2000 | Edwards |
| 6,315,773 | B1 | 11/2001 | Frey et al. |

(Continued)

OTHER PUBLICATIONS

Pelak, Victoria, S. "Ocular Motility of Aging and Dementia", Curr Neurol Neurosci Rep (2010) 10:440-447.

(Continued)

*Primary Examiner* — Mahidere S Sahle
(74) *Attorney, Agent, or Firm* — Joseph E. Maenner; Maenner & Associates, LLC

(57) ABSTRACT

In described embodiments, a device and method for diagnosing brain and neurological issues is provided. The device measures the performance of Convergence, Divergence, and binocular tracking capabilities of a subject's eyes, which can be used to determine whether a subject has experienced a brain or other neurological event.

12 Claims, 26 Drawing Sheets

(56) References Cited

U.S. PATENT DOCUMENTS

| | | |
|---|---|---|
| 6,542,081 B2 | 4/2003 | Torch |
| 7,931,370 B2 | 4/2011 | Prat Bartomeu |
| RE42,471 E | 6/2011 | Torch |
| 8,824,779 B1 | 9/2014 | Smyth |
| 9,883,814 B1 * | 2/2018 | Zarreii ................ G06F 16/9535 |
| 2009/0021695 A1 | 1/2009 | Scarpino |
| 2016/0296112 A1 | 10/2016 | Fletcher et al. |
| 2018/0153392 A1 | 6/2018 | Shibata et al. |

OTHER PUBLICATIONS

PCT/US2018/016343. International Preliminary Report on Patentability, dated Nov. 5, 2019.

* cited by examiner

SYSTEM AND METHOD FOR EVALUATING NEUROLOGICAL CONDITIONS

CROSS-REFERENCE TO RELATED APPLICATION

The present application is a Continuation of U.S. patent application Ser. No. 15/885,960, filed on Feb. 1, 2018, which is a is a Continuation of U.S. patent application Ser. No. 15/588,219, filed on May 5, 2017 and issued as U.S. Pat. No. 9,883,814, issued on Feb. 6, 2018, both of which are incorporated herein by reference in their entireties.

BACKGROUND OF THE INVENTION

Field of the Invention

The present invention is generally directed to detection and measurement of eye movement in response to visual stimulus, and more specifically to the relationship of eye movement to the brain's processing capabilities.

Description of the Related Art

It has been observed that individuals with difficulty in reacting to visual stimulus may have brain-related, visual processing and convergence anomalies. These could be as a result of chronic brain injury caused by neuro-degenerative disorders, such as Alzheimer's and other dementia or as a result of acute brain injuries such as concussions, traumatic brain injuries, strokes, TIA's, metabolic and endocrine disorders such as hyper or hypo-thyroid, diabetes, electrolyte imbalances and numerous other neurological and/or physiological disorders. Similar convergence and ocular movement anomalies can be observed in a greater extent in individuals under the influence of drugs or alcohol. Persons experiencing brain-related anomalies also exhibit certain problems with functioning effectively and learning impairments.

Convergence is a measure of a person's ability to coordinate movement of both eyes to lock onto one object. Convergence enables a person to have a seamless panoramic vision. A person does not distinguish the contribution of each eye to their vision, which results in what they see. Lack of convergence is usually exhibited by seeing two images of one real object, which results in seeing double. The efficiency and response time of the brain's convergence capability is directly related to the brain's overall physiological, neurological and chemical health and can be tested and measured by many different methods as described in this embodiment. One example would be a person's ability to follow an moving object from a first position to a second position without loss of convergence. Brain-related anomalies are related to the ability of both eyes to converge on an object at the same rate. The anomalies are directly related to the time it takes for each eye to converge on the same object. The longer it takes for both eyes to converge on an object, the more serious is the anomalous condition. This also appears to be related to a greater likelihood as to the existence of a learning impairment in a young person during the early childhood developmental years, although learning impairments may also be displayed by a person who is suffering from acute and or chronic brain injuries, such as a concussion.

Symmetry is the rate at which two eyes move to converge together with respect to an object. Latency is related to symmetry in that it is a measure of the difference in timing before both eyes converge on an object, that is the time differential before symmetry occurs. With latency, when one eye is locked on an object, there is a difference in timing before the other eye converges and locks on the same object. Thus, the greater the latency, the greater the likelihood of the existence of a deficiency in functioning ability or of a learning impairment in a person who may have acute and/or chronic brain injury.

While other devices are available to measure the convergence rate to track and record eye movements, no devices are available to accurately and quickly measure and record symmetry, convergence and latency, and relate those recorded measurements to the likelihood of the existence of a deficiency in functioning ability or of a learning impairment, which may be related to an acute or chronic brain injury. Furthermore, present methods require the executive function of the brain to control vision and convergence automatic response systems, which can create chaotic fluctuations in any device that collects data by just looking at the eyes.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The present invention provides a system that tracks the movement of the eyes as an object appears to move closer to the eye. Movement of both eyes is simultaneously detected by a single sensor. An object is presented to the eyes. The object is in the form of a light beam that is directed to a pair of fixed reflective surfaces. The light beam is reflected from each of the fixed reflective surfaces toward a second pair of movable reflective surfaces. The movable reflective surfaces are positioned by independent positioning devices controlled by a controller. The light beam is next reflected from each of the movable reflective surfaces, one in the direction of each eye, the object being the light having a first apparent distance from the eyes.

A controller with a memory continuously records the apparent distance of the object from the eyes as well as an image of both eyes. The controller directs the independent positioning devices to move the movable reflective surfaces, causing the object to appear to move closer to the eyes while the sensor sends a signal indicative of the image of both eyes as the object appears to move. The controller also calculates and records the apparent distance of the object from the eyes along with the image of the eyes. The controller also evaluates whether convergence or divergence occurs and the rate and the apparent distance at which convergence or divergence occurs.

The controller continues movement of the movable reflective surfaces while recording the image of both eyes and the corresponding apparent position of the object until divergence is detected. The recorded information is then stored by a unique subject identification for future and further evaluation.

In one embodiment, the present invention is a method of determining neurological condition in a subject. The method comprises the steps of providing a single visual target to the subject; and making the single visual target appear to represent two independent targets. The independent targets are movable independently.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION

Figure 1:
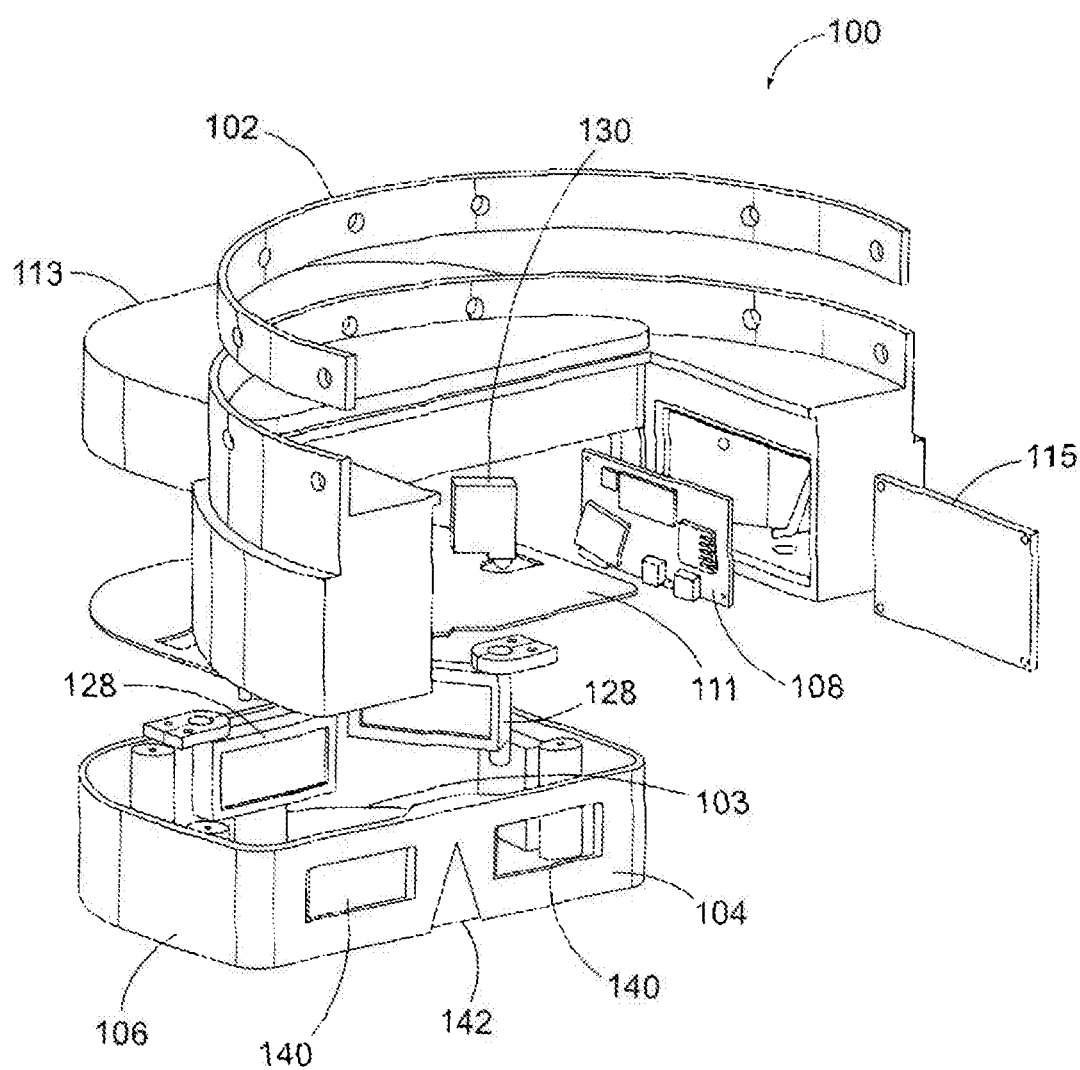
FIG. 1 is a rear exploded perspective view of the headpiece of the present invention.
Figure 2:
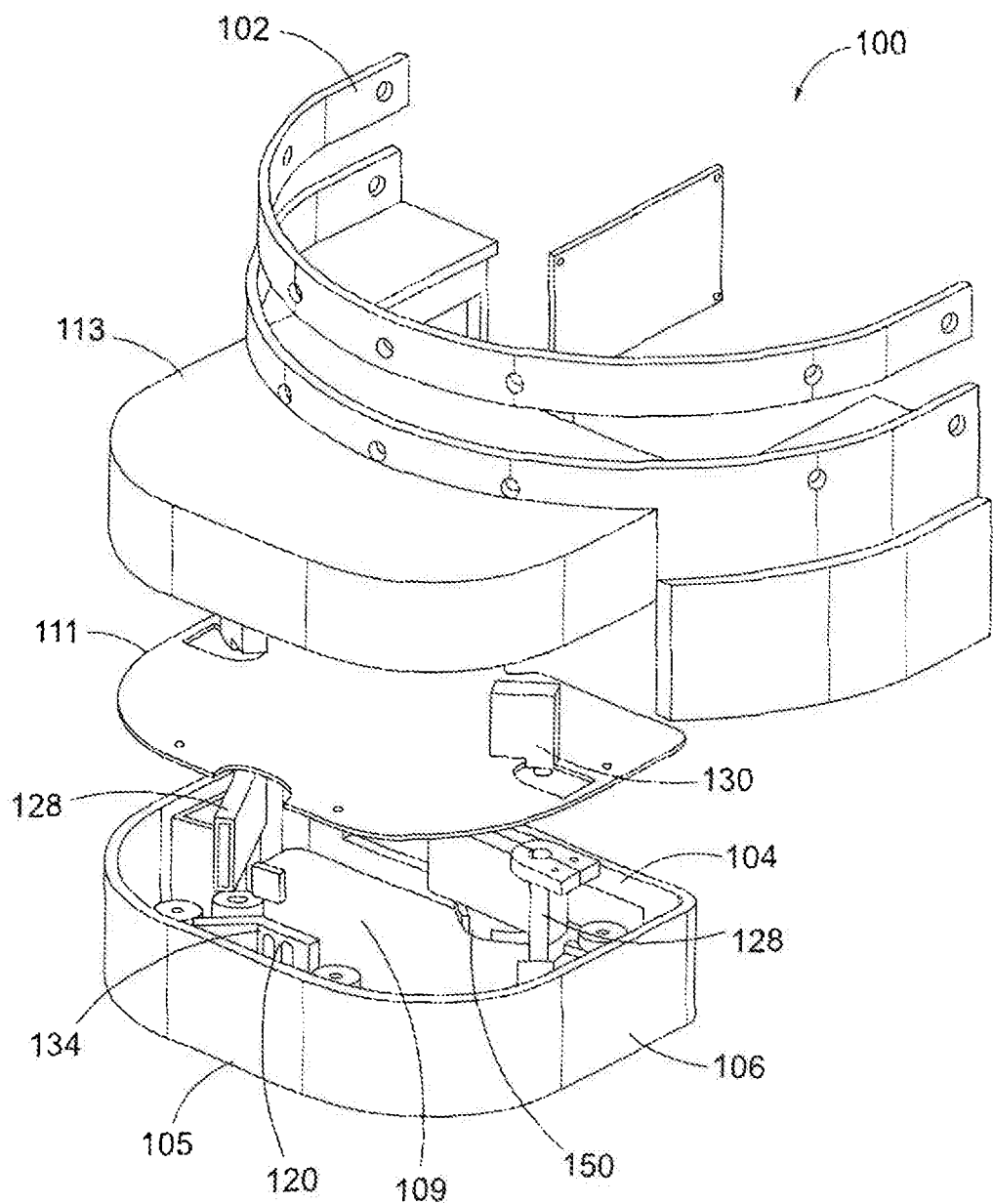
FIG. 2 is a front exploded perspective view of the headpiece of the present invention.
Figure 3:
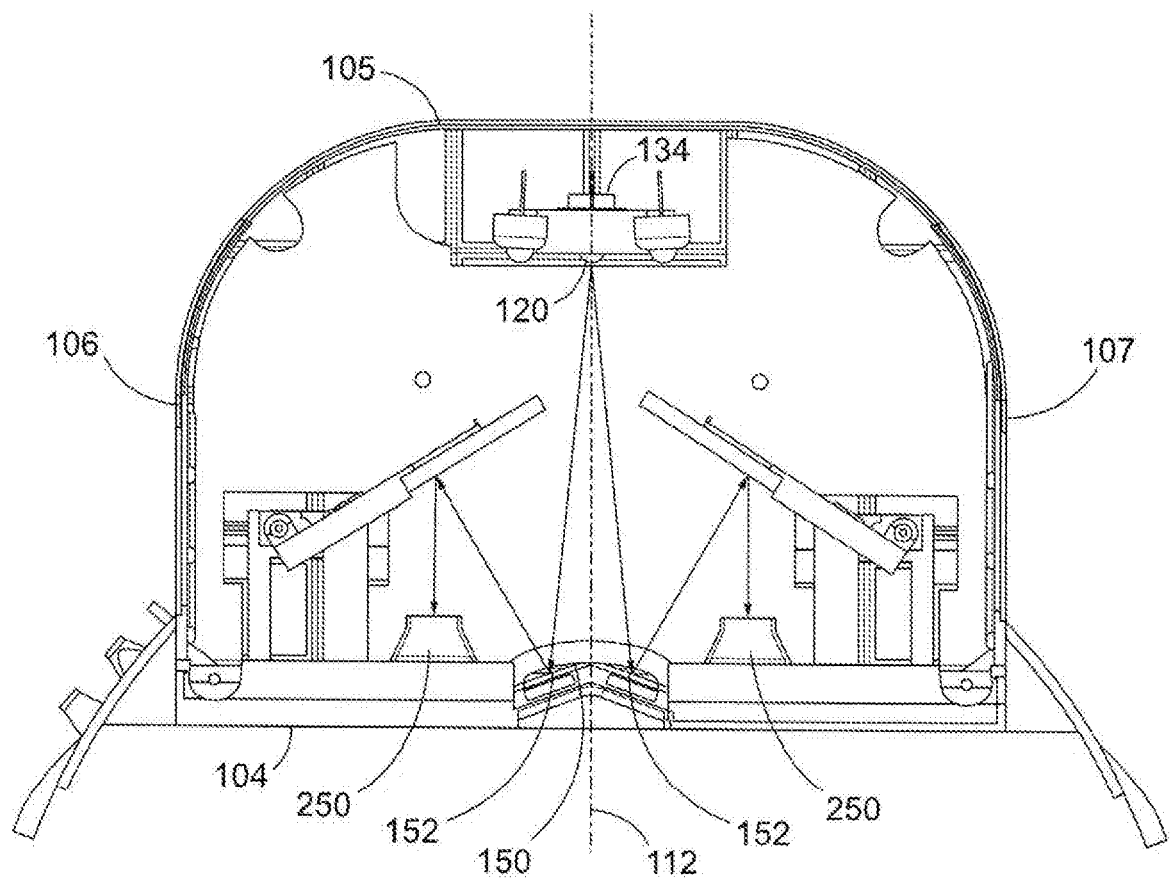
FIG. 3 is a top plan view of a compartment used with the headpiece shown in FIGS. 1 and 2.
Figure 4:
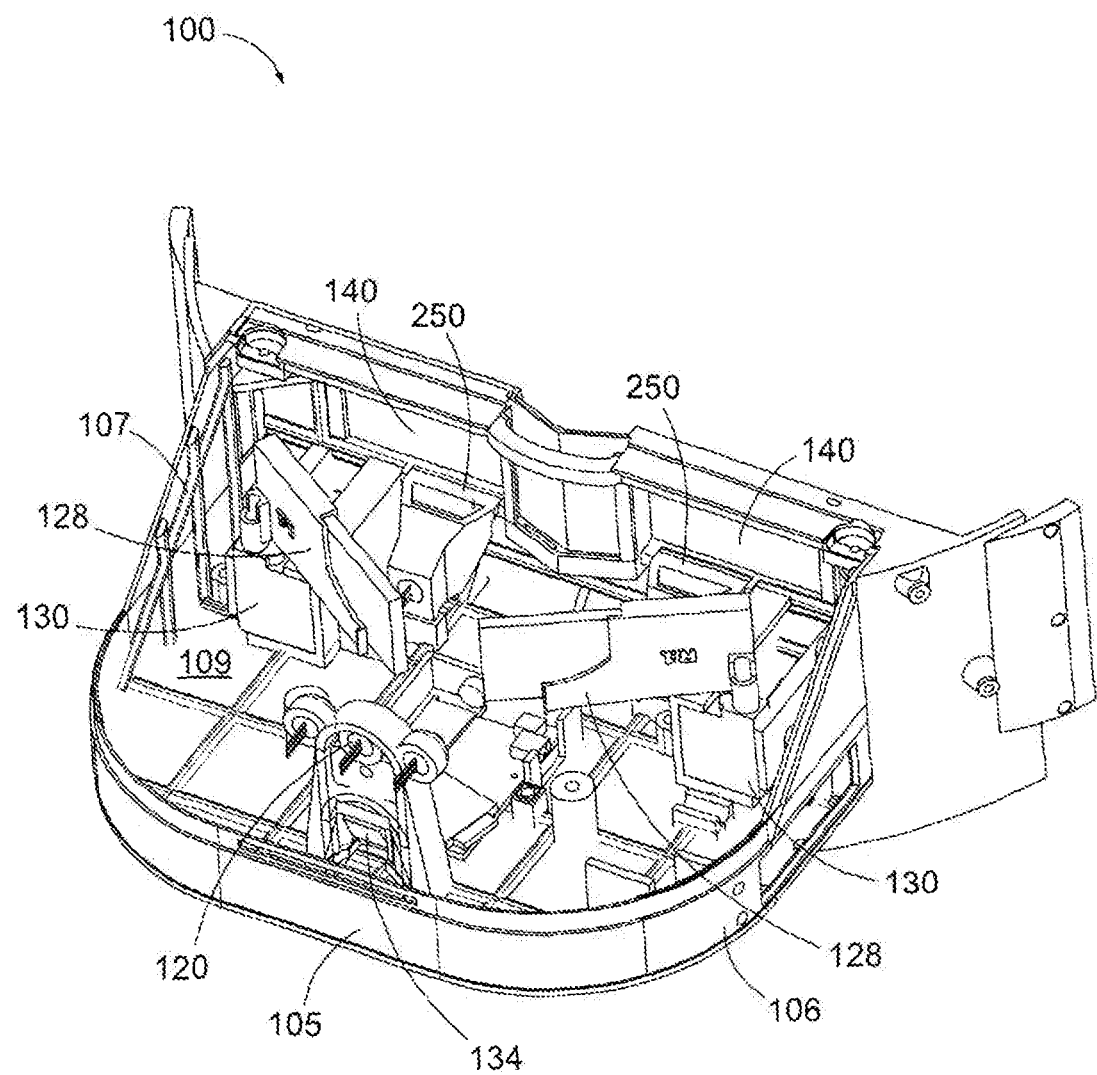
FIG. 4 is a perspective view of an interior of the compartment of FIG. 3.
Figure 5:
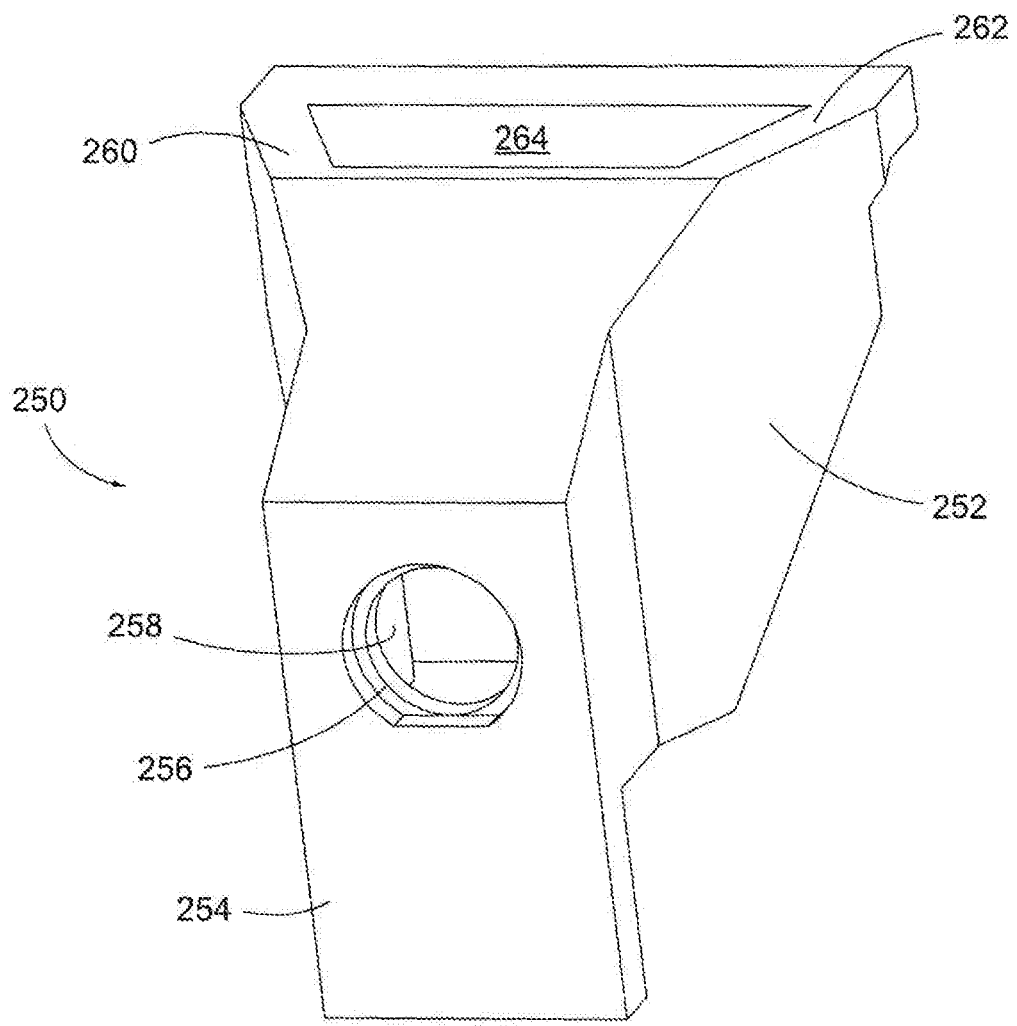
FIG. 5. is a perspective view of a light diffuser used with the device shown in FIG. 1.
Figure 6:
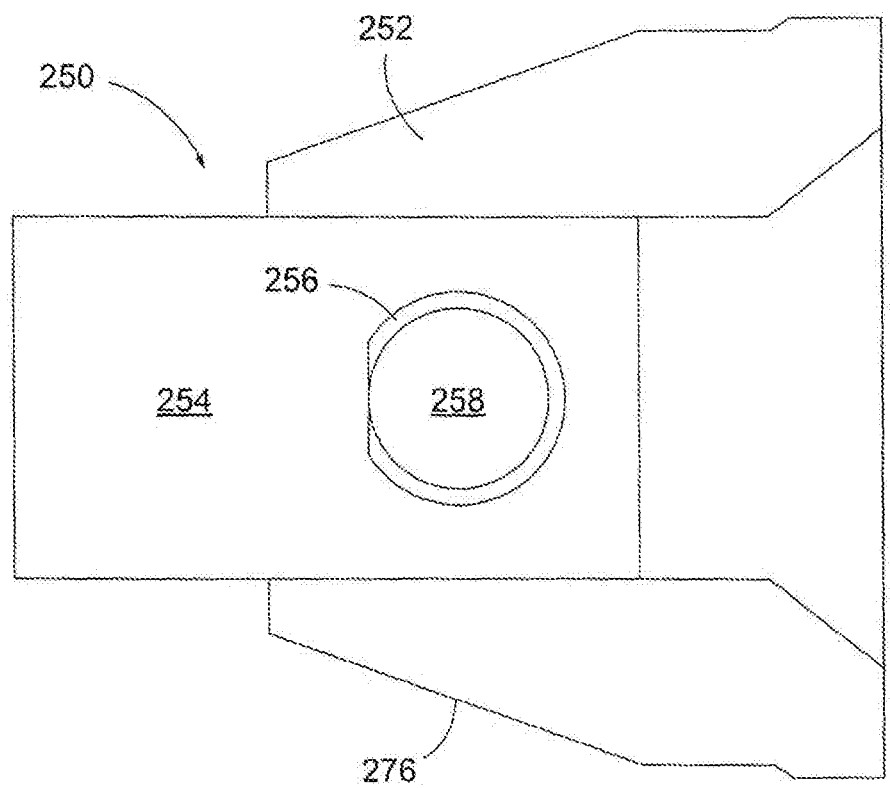
FIG. 6 is a top plan view of the diffuser shown in FIG. 5.
Figure 7:
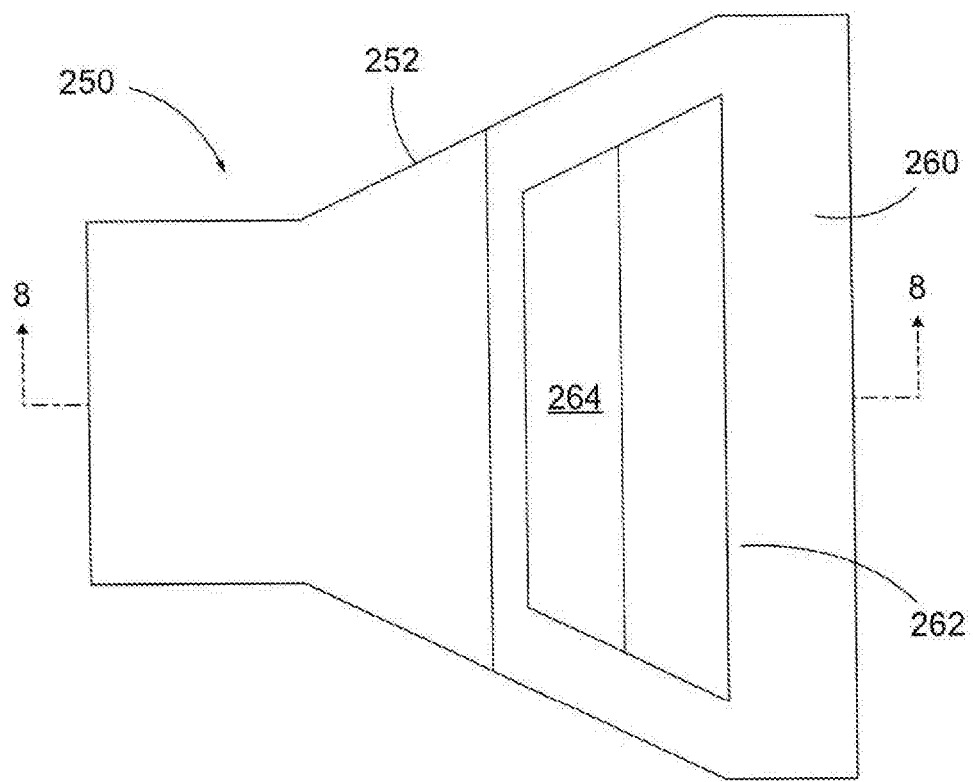
FIG. 7 is a front elevational view of the diffuser shown in FIG. 5.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "event" is used to mean an occasion or experience that changes a subject's brain or neurological status from one condition to another. Such an "event" can be a blow to the head, possibly resulting in a concussion; a stroke or a mini-stroke: or other such experience that changes brain and/or other neurological functioning. Additionally, the term "proximal" is defined as a direction closer to the eyes of a subject being evaluated and "distal" is defined as a direction away from the eyes of the subject being evaluated.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

The executive function in the brain is a process that enables multi-tasking, the ability to plan and focus attention on an issue, and make plans for action including what the eyes will focus on. The automatic response portion of the brain controls vision and convergence (which is coordination of the two eyes) that results in a seamless panoramic view seen by a person. A person is unaware of which eye produced which portion of what they are seeing. The convergence control system is one of the most complex functions performed by the brain. The brain's performance is based on the quality of physiological, neurological and chemical processing capabilities of the brain. Since this is such an essential function, evolution has built in many redundant sub-functions to guarantee performance of vision. Loss or reduced performance of any of these redundant sub-functions will degrade the overall performance of convergence and vision. This reduced performance, however, increases the processing load on remaining redundant sub-functions with an attempt to compensate for the loss and try to meet the real time demand that is placed on the convergence and vision.

To meet the real time performance requirements necessary to protect and keep the person alive and functioning successfully in society, the automatic response convergence and vision system attempts to execute all commands that it receives from the executive function. For example, a person's eyes will see whatever the person wants to see.

Any deficiencies that occur in the brain due to various factors (trauma, disease, or drugs) will affect the performance of this system; however, as long as this system is meeting the real time performance requirements, no change is noticed externally by physicians or others. The person will start noticing some decline in their ability to concentrate, or to carry out visual tasks. These deficiencies are only taken seriously after the visual control system no longer can meet the real time requirements, which may result in the person being unable to function properly. At that point, major not-easily reversible damage has occurred in neurological and physiological portions of the brain.

The present invention generates conditions that momentarily disengage the convergence "circuits" and examines each eye's control capabilities and responses independently. The present invention also is capable of disengaging the executive function momentarily during the various test conditions, thereby eliminating the chaotic movements of the eyes during test conditions, resulting in a much more clear detection of anomalies. Its methods are non-invasive to the person.

By way of example, the present invention can be used for detection and classification of the severity of an acute brain injury, such as a concussion, in a timely and accurate manner. The present invention can also provide diagnostic and follow up data to track the progress of a person's condition.

The present invention can also be used as an example, for early detection of the onset of chronic brain injuries such as Alzheimer's and other dementia. In the early stages of Alzheimer's a person may function independently. He or she may still drive, work and be a part of social abilities. Despite this, the person may feel that he or she is having impaired ability to concentrate, memory lapses such as forgetting familiar words, location of everyday objects or losing the ability to navigate. At this stage of the disease, the person is usually a self-advocate, and when seeking consultation complaining with non-specific neurological symptoms, a physician may not make a diagnosis, possibly due to lack of availability of objective testing, and might not prescribe neuro-supportive pharmaceuticals. The person at this early stage of the disease would greatly benefit from neuro-supportive pharmaceuticals and other therapies to maintain the quality of life and delay the onset of the very harsh late stage of the disease.

With the current methods of psychological evaluations as a standard for detection of Alzheimer's and other neurodegenerative diseases, the person must reach a "point of no return" where they have chronic brain injury to the point that they cannot perform normal neurological functions effectively. This is "the point of no return", since most likely non-reversible physical damage has been sustained by the brain.

With the use of this invention, the latency of ocular motor and convergence capabilities of the brain in a person are measured with higher accuracy and finer scale. This will allow detection of performance degradation much earlier and before significant permanent injury to the brain has occurred, thereby increasing the probability of accuracy and timeliness of a diagnosis, significantly earlier than current methods. With proper treatment and use of neuro-supportive pharmaceuticals and therapies, a person at this point has a far greater chance of having a higher quality of life and greatly delaying the onset of the late stage of the disease.

The present invention can also be used as an example, in conjunction with drug development for neurodegenerative diseases. The device allows a clinician or device control software to have a baseline and allows the clinician or device control software to measure minute changes that current methods of psychological evaluation cannot detect. Clinical trials incorporating the inventive device can aid drug development and other developments in the medical field that measure the changes in patients on a more defined scale.

The present invention can also be used as an example, for educational assistance, such as throughout the K-12 grade levels. During the early development stage of life, if convergence "circuits" are not operating at optimum levels and have latency, it creates various levels of sensory overload that can cause anxiety and inattentiveness that will cause a negative impact on a person's ability to learn. That anxiety may make a student appear unsuccessful because he/she does not do well on standardized tests. The present invention can be used to combine the testing of reading and math with the measuring of eye convergence anomalies. With the use of the therapy mode of the present invention, as the speed of convergence is increased and latency is reduced, the reading and math capability of students can be improved. A correlation can be seen between improved reading and convergence speed. Learning abilities may not be disabilities but are instead inefficiencies. In those cases, the child's condition can be improved and driven closer to an acceptable grade level.

The inventive device and method are used to remove the executive function of a subject's brain out of the process of determining whether the subject may be experiencing a brain or other neurological event, either permanent or temporary. This device enables physicians and others to measure the efficiencies of these systems and intervene at a much earlier point and stop or reduce further damage.

The present invention provides a headpiece that fits over the head of a subject so that the eyes of the subject may be evaluated. The headpiece includes a single sensor that follows the movement of both eyes. The headpiece also includes a light source that is presented to the eyes. Also within the headpiece is first pair of reflective surfaces, the first pair of reflective surfaces being fixed, and a second pair of reflective surfaces which are movable. The second pair of reflective surfaces may be moved by any mechanical, electrical, electromechanical mechanism or by optical manipulation.

In an exemplary embodiment, a pair of servos, also located within the headpiece, is the current electromechanical mechanism utilized to control the reflective surfaces. One servo is in communication with each mirror. In another embodiment, an actuator may be used to control the reflective surfaces. The mechanisms, whether mechanical, electrical or electromechanical, are in communication with a controller which directs their movements and their rate The headpiece is in communication with a controller. The controller may be positioned within the headpiece, for example on a circuit board, but may be positioned elsewhere. For example, the controller may be a general purpose computer in communication with the headpiece that is programmed to control the headpiece with its own memory or a module that is part of a larger controller with a dedicated memory. The location of the controller and whether it is a dedicated device is not an important aspect of this invention, although the controller must be in communication with the headpiece as well as the mechanisms controlling the reflective surfaces or individual light sources when individual light sources are directed at the subject's eyes. When the controller is positioned within the headpiece, the controller stores information from evaluation within a controller memory. In an exemplary embodiment, this stored information is communicated to a remote device at some time to identify the subject and store the information from the evaluation in a permanent storage device for subsequent analysis.

The information can be communicated from the controller to the permanent storage device either wirelessly, a direct wired connection or a combination thereof. The evaluation is initiated by the controller when located within the headpiece initiates the test, for example, by an external stimulus, for example, on command by a remote electronic signal or by the push of a button located on the headpiece. The controller may include a program that activates the light beam, which is stationary, and is in communication with the servos in the preferred embodiment. The controller program controls movement of the servos in accordance with a preselected sequence of motions. The controller is also in communication with the single sensor, the single sensor providing a signal indicative of the movement of the eyes with the preselected sequence of motions which also is stored in the controller memory. The controller may also process the information either before or after storage in the memory in order to evaluate the response of the subject to an apparent movement of the light beam produced by the light source. When two light beams are used instead of movable reflective surfaces, the controller controls the movement of the light beams.

In an exemplary embodiment, the controller is positioned remotely from the headpiece. The controller and the headpiece may be in communication wirelessly, via direct wired connection or a combination thereof. The evaluation is initiated by the controller, activating the light source, which is stationary, producing the light beam. The controller is also in communication with the servos. A controller program controls movement of the reflective surfaces by controlling movement of the light beams, in the exemplary embodiment, by controlling movement of the servos in accordance with a preselected sequence of motions. The movement of the reflective surfaces provides an apparent motion of the light source. There may be more than one controller program, each program providing a different preselected sequence of motions, the operator selecting the desired program. The controller is also in communication with the single sensor, the single sensor providing a signal indicative of the movement of the eyes in response to the apparent motion of the light source, which is stored in the controller memory. The controller may also process the information either before or after storage in the memory in order to evaluate the response of the subject to an apparent movement of the light beam from the light source.

Regardless of the physical location of the controller, the headpiece of the present invention provides an apparent movement of an object, here the light beam produced by the light source by movement of the reflective surfaces within a small, comfortable, compact, lightweight device that is readily attached to the head of a subject. The head piece is adjustable to accommodate subjects having varying head sizes. Although an exemplary embodiment of the present invention generates a light source producing a light beam, the target object may be any image. It will be understood, however, that the image must be illuminated so that the image can be seen by the eyes.

Further, it will be understood that, in the present invention, movement of the light beam results in apparent movement of the light source, which is tracked by the subject. In the exemplary embodiment, apparent movement is accomplished as the light beam is reflected from the reflective surfaces as they are moved by their positioning devices in response to instructions from the controller, so that movement of the light beam and movement of the light source may be used interchangeably. In an exemplary embodiment, the light source is an LED light, such as a variable wavelength between about 400 and about 700 nm, a variable lumen between about 110 and about 650 lumens, and variable wattage between about 75 and about 120 milliwatts. This type of LED allows for evaluation using a variable intensity and variable colors which is useful for individuals suffering from reduced color sensitivity.

Once a test is initiated, in the exemplary embodiment, a light beam from the light source is directed toward the first pair of reflective surfaces. While the beam may be split, the first pair of reflective surfaces is arranged to receive the beam from the light source when the beam is not split and reflect the light in different directions. The light beam is reflected from the first pair of reflective surfaces toward the second pair of reflective surfaces. The light from the second pair of reflective surfaces is reflected toward the eyes. The sensor is positioned to observe the eyes. The servos, in accordance with preprogrammed instructions from the controller, then move the second pair of reflective surfaces resulting in a change of the reflection pattern perceived by the eye. This change in the reflection pattern results in an apparent movement of the light source toward or away from the subject's eyes, even though the actual distance of the light source from the subject's eyes is constant.

The sensor detects any eye movement in response to the change in the reflection pattern and the apparent movement of the light source. The sensor sends a signal indicative of the eye movement which is recorded in the controller memory. In accordance with the programmed instructions, the servos continuously move the second pair of reflective surfaces, causing a continuous change in the reflection of the light beam, resulting in an apparent continuous movement of the light source at a predetermined rate. The sensor continuously monitors the position of the eyes in response to reflection of the light beam, the results being continuously received by the controller and stored in controller memory.

The test may be terminated either after a predetermined time for the test or when the sensor detects predetermined eye movement has occurred, the predetermined eye movement indicative of results. Thus, the test may be terminated when either convergence or divergence is detected. Convergence and divergence may describe the same results but depend on where the test is initiated. Divergence occurs when an object at a distance moves toward the subject and is a distance at which the object no longer appears as a single object to the eyes but rather as two objects, one to each eye. Convergence occurs when an object close to the subject initially appears as two objects, so as the object moves away from the subject, it is the distance at which the eye detects the object as a single object.

Referring now to FIGS. 1-4, an exemplary embodiment of a headpiece 100 used to perform the above-described tests, as well as other tests that will be described herein, is shown. In FIG. 1, a headpiece 100 is shown having an adjustable headband 102, which is partially shown. The headband 102 extends around the head of a subject. While a headband 102 is shown, those skilled in the art will recognize that headband 102 can be omitted, and headpiece 100 can be mounted on a stand (not shown) and a subject can lean in to headpiece 100 for evaluation.

Headpiece 100 includes a compartment 103 into which a subject (not shown) looks. Compartment 103 is defined by a proximal wall 104, a distal wall 105, sidewalls 106, 107 that extend between proximal wall 104 and distal wall 105, as well as a floor 109 and a ceiling 111. A central axis 112 extends between proximal wall 104 and distal wall 105. Compartment 103 is a closed box that is configured to block any extraneous light from entering compartment 103 that might distract the subject from internally supplied lighting.

Electronics and power to operate headpiece 100 can be located above ceiling 111 so that such equipment is out of view of the subject. A circuit board 108 is mounted in an equipment housing 113 located above ceiling 111 and is covered by a removable circuit board cover 115. Batteries (not shown) and/or an electrical power connection can be located in equipment housing 113 as well.

Proximal wall 104 includes a pair of spaced apart eyeslits 140 for the subject's eyes to peer through into compartment 103 and a nose bridge 142 located between eyeslits 140 (along central axis 112) to rest on the subject's nose, as well as to align headpiece 100 with the subject's eyes.

A reflecting reflector 150 is mounted on the interior of proximal wall 104 between eyeslits 140 and along central axis 112. Reflecting reflector 150 includes two reflecting surfaces 152 that extend at an angle relative to central axis 112 to redirect light from light source 120 at an oblique angle relative to central axis 112.

A light source 120, such as an LED, is located at a distal end of headpiece 100, proximate to distal wall 105 and along central axis 112, is directed toward proximal wall 104 and is used as a target for the subject to focus on while the subject is being evaluated. Light source 120 can be a variable wavelength light source so that different wavelengths of light can be emitted from light source 120, depending on the type of evaluation to be performed using headpiece 100.

Light source 120 is mounted so that the subject can see light source 120 with both eyes when peering through eyeslits 140. In an exemplary embodiment, light source 120 is centered along distal wall 105 and is equidistant from each eyeslit 140.

A sensor 134, such as a CCD camera 134, is also located at distal wall 105 and is directed to be able to capture and record the subject's eyes through eyeslits 140. Camera 134 is electronically connected to circuit board 108, which controls camera 134 and receives data and video information recorded by camera 134. Alternatively, camera 134 can be operated via a separate controller (not shown). The use of a single camera 134 allows a clinician or device control software to monitor and measure both of a subject's eyes simultaneously with a single scan, which allows for proper alignment between the eyes and to measure alignment and measurement of the movement direction of both eyes, with direct correlation between both eyes.

A pair of pivoting panels 128 is mounted generally in the middle of compartment 103, on opposing sides of central axis 112 of compartment 103. Each panel 128 is located so that, when panel 128 is rotated to a first position, panel 128 blocks light from light source 120 from being viewed by a subject's eye on that side of the central axis and, when panel 128 is rotated to a second position, panel 128 is rotated out of the line of sight from eyeslit 140 to light source 120 so that the eye looking through eyeslit 140 can view light source 120.

In an exemplary embodiment, panels 128 can be pivoted through an arc of about 90 degrees, although those skilled in the art will recognize that panels 128 can pivot through a different range. Panels 128 are pivotable such that light from light source 120 can reflect from reflecting surfaces 152 of reflector 150 and onto panels 128 when panels 128 are in the first position as well as when panels 128 are rotated through an arc less than the full arc of rotation.

Panels 128 are each independently moved by a respective servo motor 130 located in equipment housing 113 and electronically connected to circuit board 108. An output of servos 130 extends through equipment housing 113 and into compartment 103 for connection to panels 128. Each servo 130 is independently operable depending on the desired use of panels 128.

In a first embodiment, panels 128 are reflective surfaces that are used for when convergence is not achieved and different distances have to be mimicked to determine convergence. In a second embodiment, panels 128 are opaque surfaces that are used to optically occlude light source 120 and determine that the convergence ability of the brain is not operating efficiently, as will be discussed later herein. Panels 128 are removable and can be interchangeable as reflective surfaces or opaque surfaces.

Optionally, in order to provide sufficient light internal to headgear 100, referred herein as "ambient light", for camera 134 to be able to record the subject's eyes, a light is provided. The light is out of the direct line of sight of the subject's eyes, regardless of the direction in which the subject's eyes move. In order to reduce any distraction to the subject resulting from ambient light, a light diffuser 250 can be used to diffuse the light within headgear 100 and can be located below each eyeslit 140, with a light 251 being provided for each light diffuser 250. Alternatively, those skilled in the art will recognize that diffusers 250 can be located above or beside each eyeslit 140.

An exemplary light diffuser 250 is shown in FIGS. 5-9. Light diffuser 250 diffuses a light 251 that is mounted above light diffuser 250. Light 251 is used to illuminate the test subject's eyes so that camera 134 can record the test subject's eyes.

Diffuser 250 includes an opaque or translucent body 252 having a generally planar input surface 254 on one side of body 252. Input surface 254 has a light input end 256 with a generally circular light input opening 258 formed therein to accept light 251 without light from light 215 escaping diffuser 250 and into compartment 103 above light diffuser 250. Lights 251 can be powered and controlled by circuit board 108.

Body 252 also has a generally planar output surface 260 that extends on a second side of body 252 generally orthogonally to input surface 254. Output surface 260 has a flared light output end 262 with a light output opening 264 formed therein. Light output opening 264 is larger than light input opening 258 and can be generally quadrilateral in shape, more specifically, a rhombus.

Figure 8:
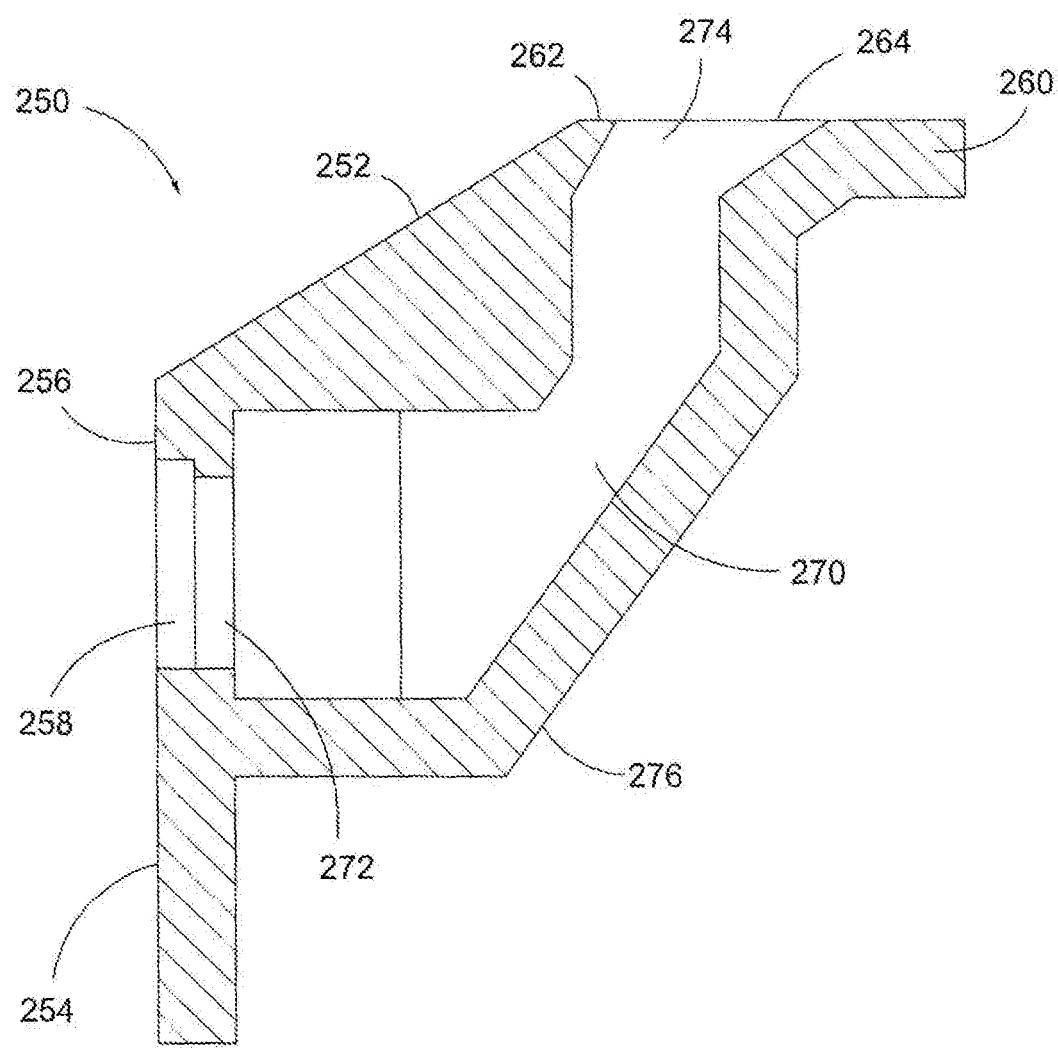
FIG. 8 is a sectional view of the diffuser shown in FIG. 7, taken along lines 8-8 of FIG. 7.

A light passage 270 extends through body 252 between light input end 256 and light output end 262 and is in communication with light input opening 258 and light output opening 264. Light passage 270 extends along a non-axial path so that any light source, such as light 251, at light input end 256 cannot be directly viewed from light output end 262. In an exemplary embodiment, light passage 270 defines a tortuous path with a plurality of non-co-axial adjacent path portions, as shown in FIG. 8. Those skilled in the art, however, will recognize that light path 270 can have other profiles, just as long as any light source at light input end 256 cannot be directly viewed from light output end 262.

To optimize the effect of light diffuser 250, light passage 270 has a first area 272 at light input end 256 and a second area 274, larger than the first area 272, at light output end 262 such that light passage 270 expands from a generally circular opening at light input opening 258 to a generally quadrilateral opening at the light output opening 264.

Figure 9:
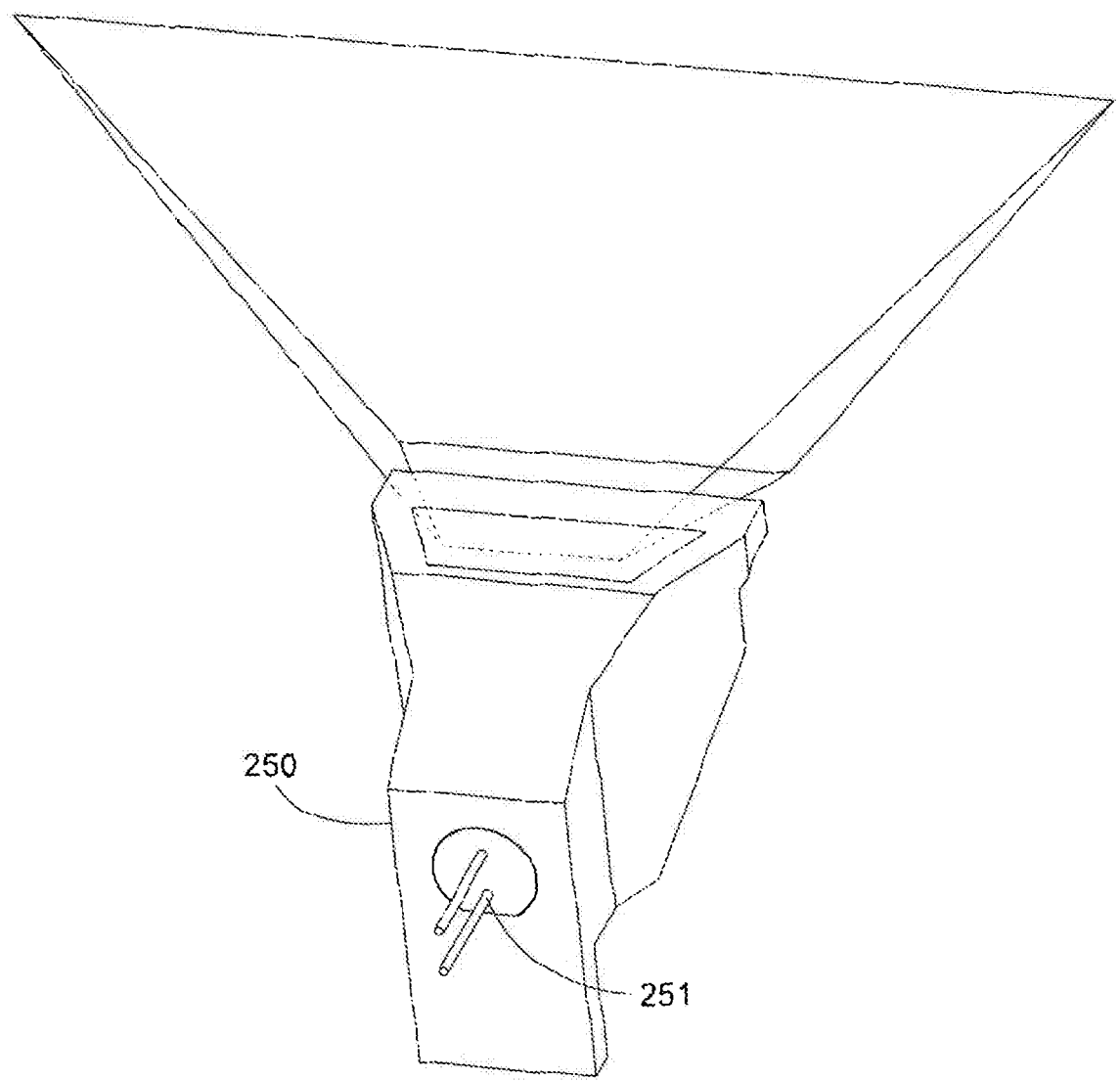
FIG. 9 is a perspective view of the diffuser of FIG. 5, showing a light beam emanating from the diffuser.

Light diffuser 250 also includes a mounting surface 276 extending obliquely between input surface 254 and output surface 260. Mounting surface 276 is generally planar to allow light diffuser 250 to be fixedly mounted to headpiece 100 above eyeslit 140 so that light output opening 264 directs light through light diffuser 250 vertically downwardly to provide light for a subject looking through eyeslit 140, without the subject being able to actually view the light source, which can distract the subject during evaluations. A light diffuser 250 is provided for each eyeslit 140. As shown in FIG. 9, a light beam emanating from diffuser 250 extends in a broad area, much larger than the diameter of light 251 that generates the light beam.

Headpiece 100 can be used to evaluate different neurological factors based on convergence or non-convergence of the subject's eyes, as well as the amount and rate of pupil dilation of the subject's eyes. Convergence or non-convergence can be an indication of an acute brain injury, such as a concussion. Additionally, the use of headpiece 100 over an extended period of time (i.e., once per year for a period of years) can provide an indication of a chronic brain disorder, such as the onset of Alzheimer's disease, or other dementia.

With a concussion, the ability to converge at same rate is reduced and the ability to move from one target to another takes longer time. This reduction can be evidenced in football players, hockey players, or players in other contact sports who have suffered at least one, and possibly multiple, concussions throughout their careers. It would be beneficial to perform baseline testing on such athletes prior to their playing careers to establish the baseline and to determine any changes over time or after concussions or suspected concussions. Using device 100 in an occlusion mode can determine the severity of a concussion.

Device 100 can also be used to evaluate whether a subject has undergone any type of physiological damage, resulting in diverging eyes; neurological damage, resulting in slower response rate; or chemical damage, also resulting in slower response rate. Further, device 100 can be used to evaluate the potential for chronic neurodegenerative diseases, such as Alzheimer's dementia, which can result in a slowly reduced rate of convergence.

Figure 10:
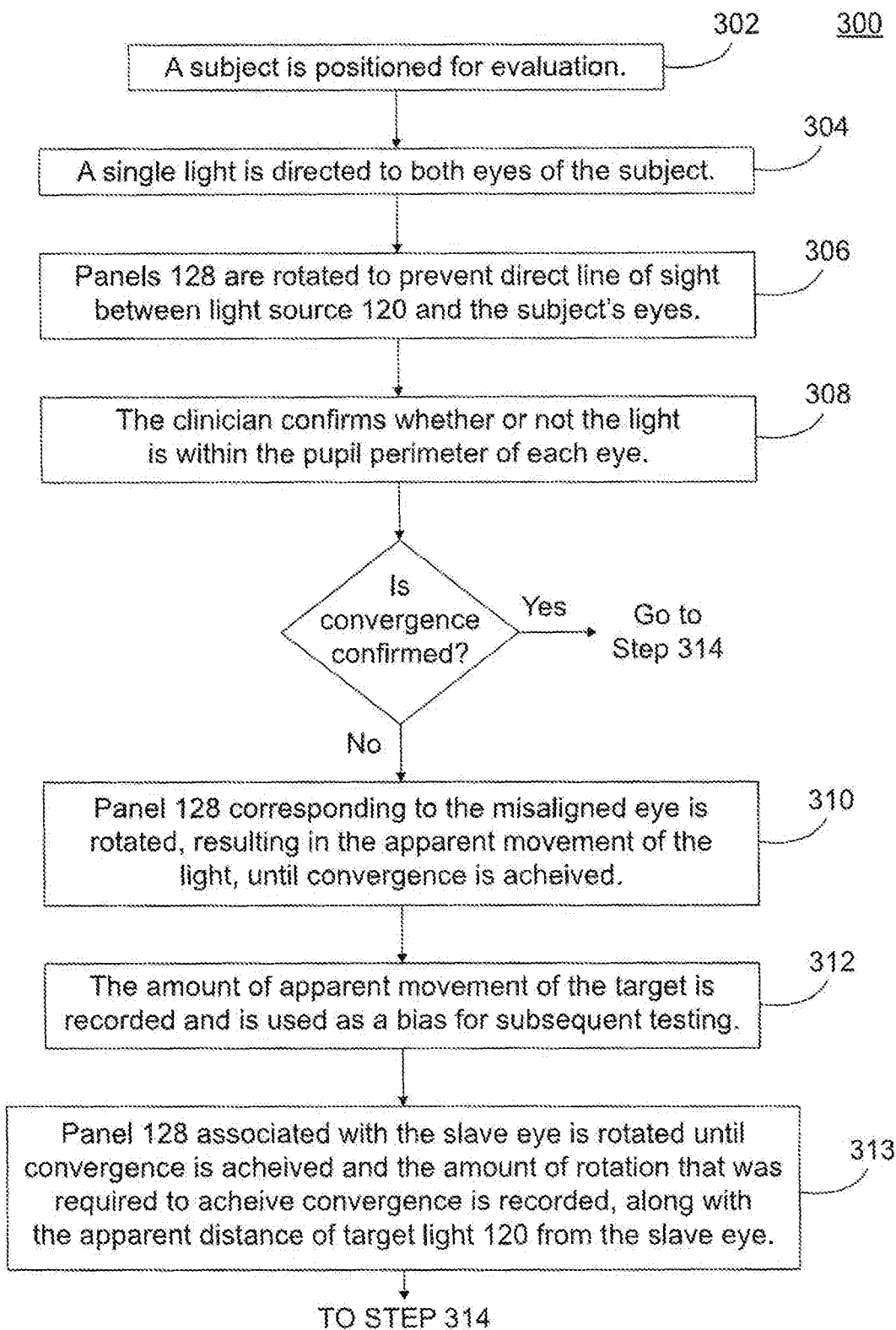
FIGS. 10 and 11 are a flowchart showing an exemplary method of using the device of the present invention.
Figure 11:
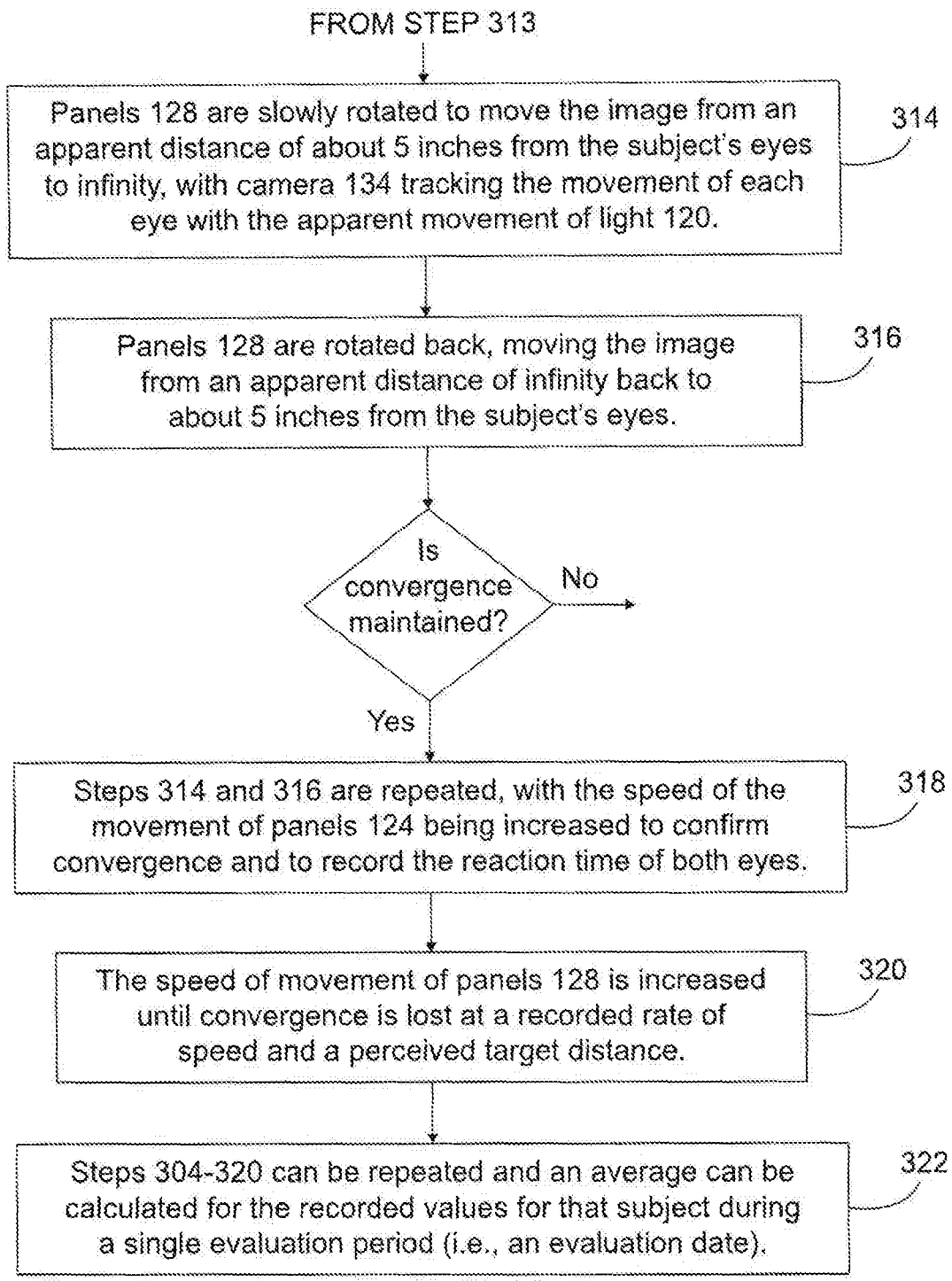

Headpiece 100 can be used to evaluate different neurological conditions. Referring now to flowchart 300 shown in FIGS. 10-11, in step 302, a subject is positioned for evaluation, which can include placing headpiece 100 over the subject's head and adjusting headband 102 so that headpiece is snugly retained on the subject's head. Camera 134 is locked onto both eyes. The distance from the eyes to camera 134 is fixed. For this test, panels 128 include a reflective surface on a proximal side of each panel 128.

In step 304, a single target in the form of a light is directed to both eyes of the subject. In an exemplary embodiment, the single target can be light source 120. Light source 120 can be used as a target for the subject to view with both eyes. A separate light source 251 is used to illuminate both eyes so that camera 134 can record the motion of the eyes during the procedure. Light sources 251 can be independently operated so that one light 251 can be turned on while the remaining light 251 can be turned off, depending on the evaluation being performed.

Figure 12:
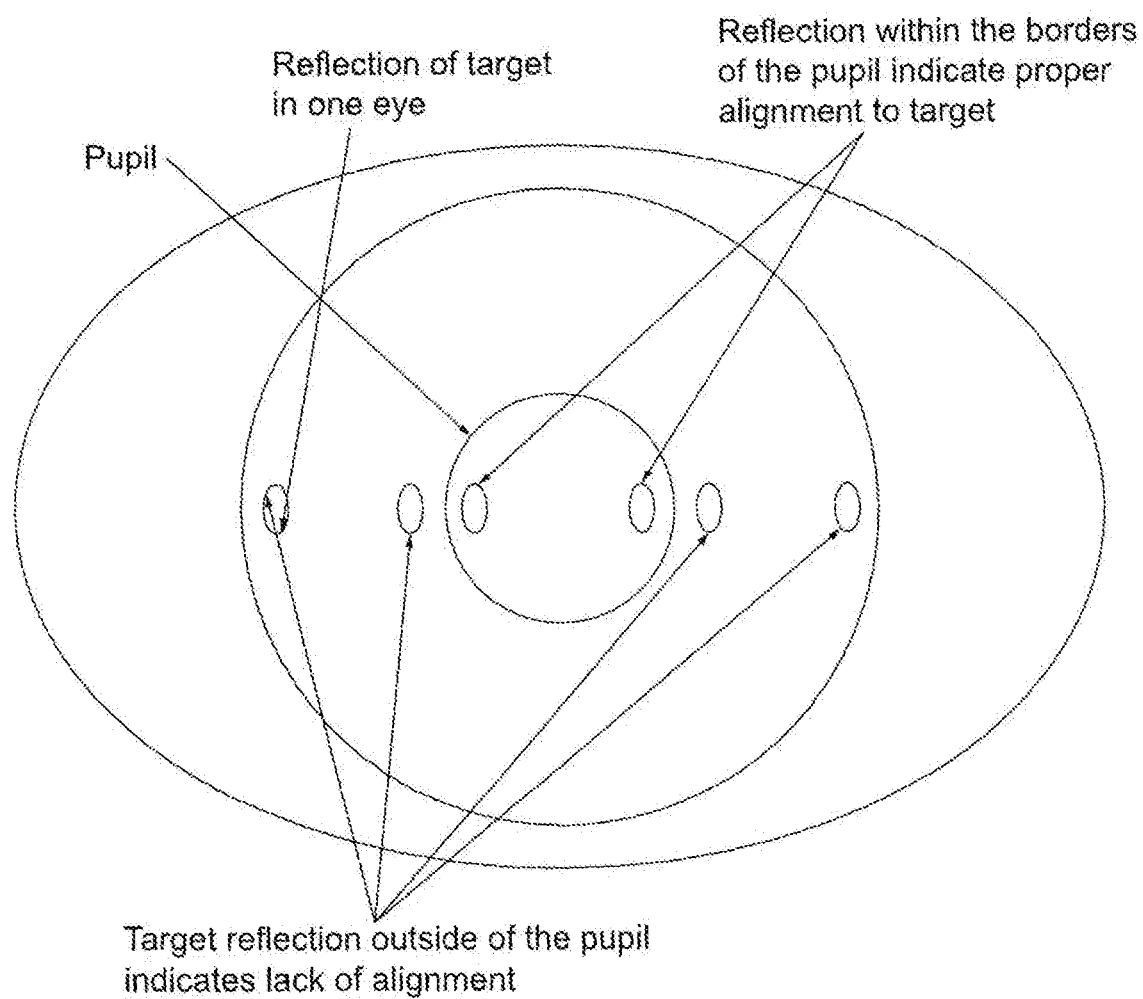
FIG. 12 is an enlarged view of an alignment confirmation system to indicate proper alignment of the pupil to a target.

In step 306, panels 128 are rotated to prevent a direct line of sight between light source 120 and the subject's eyes. The light from light source 120 reflects from reflecting surfaces 152 and onto panels 128. In step 308, the clinician or device control software confirms whether or not the light is within the pupil perimeter of each eye. By way of example only, FIG. 12 shows different examples of the light within or outside of the pupil perimeter. If convergence is not confirmed, in step 310, panel 128 corresponding to the misaligned eye is rotated, resulting in the apparent movement of the light, until convergence is achieved. In step 312, the amount of apparent movement of the target is recorded and is used as a bias for subsequent evaluation.

Figure 13:
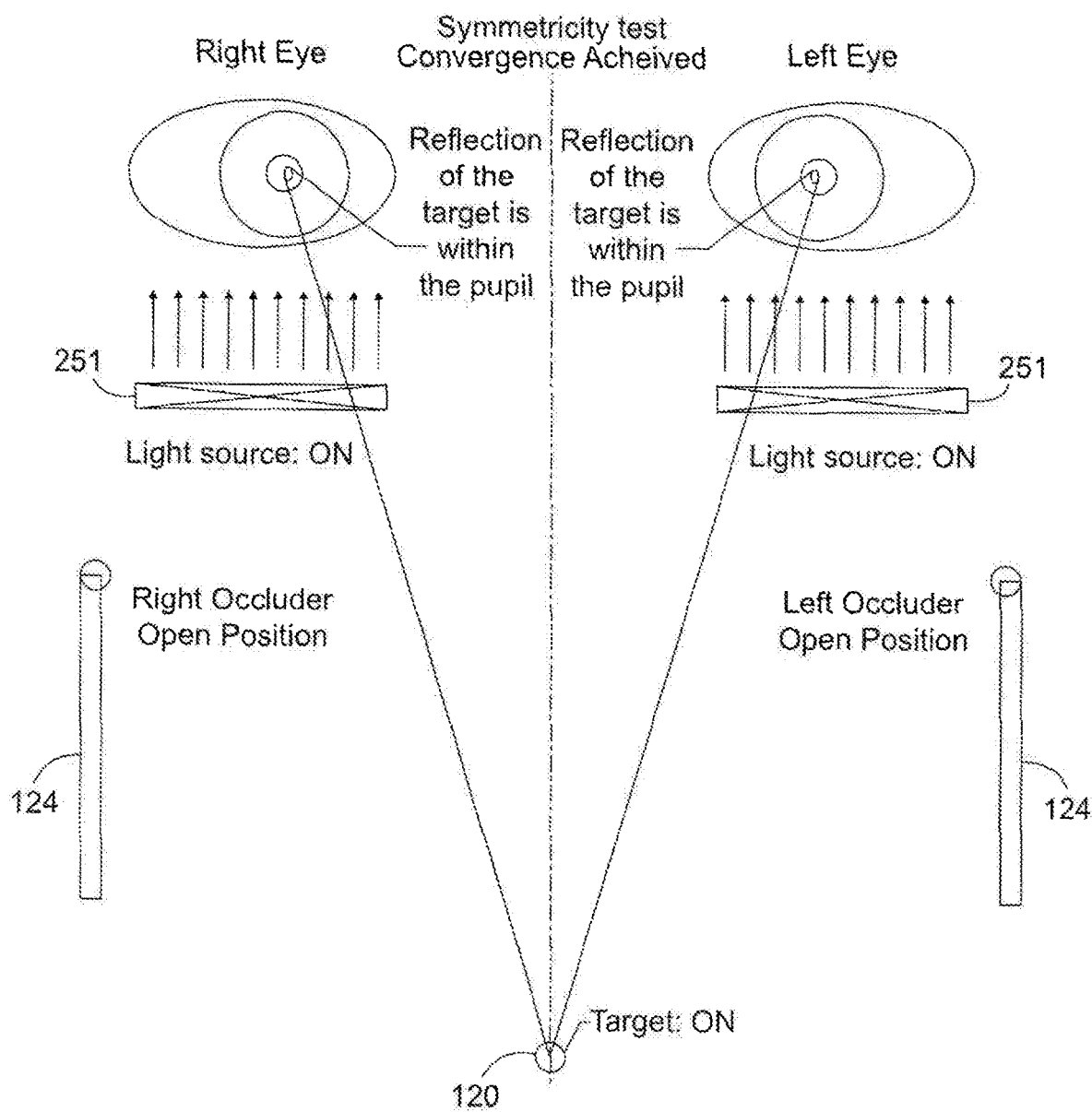
FIG. 13 is a schematic view of a symmetricity test showing both eyes converging on a target.

Convergence is shown in FIG. 13. If convergence was not achieved, the eye that shows the reflection of target light 120 within the perimeter of the pupil is called the "master" eye, and the eye that does not shows the reflection of target light 120 within the perimeter of the pupil is called the "slave" eye. In step 313, panel 128 associated with the slave eye is rotated until convergence is achieved (the target light 120 is reflected within the perimeter of the pupil of both eyes) and the amount of rotation that was required to achieve convergence is recorded, along with the apparent distance of target light 120 from the slave eye.

Figure 14:
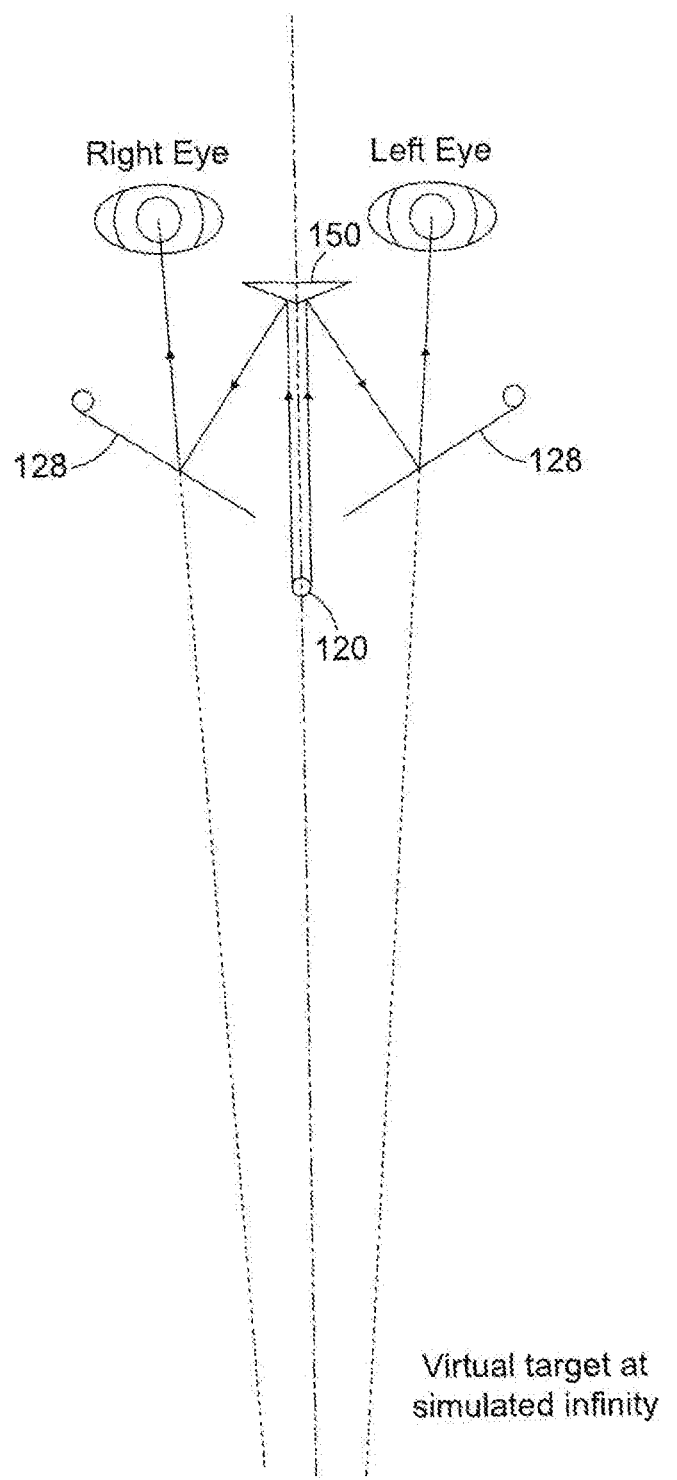
FIG. 14 is a schematic view showing a virtual target at an infinite distance from a subject.

In step 314, panels 128 are slowly rotated to move the image from an apparent distance of about 5 inches from the subject's eyes to infinity, as shown in FIG. 14, with camera 134 tracking the movement of each eye with the apparent movement of light 120. In step 316, panels 128 are rotated back, moving the image from an apparent distance of infinity back to about 5 inches from the subject's eyes. During steps 314 and 316, camera 134 records the movement of the subject's eyes and determines if convergence was achieved throughout the test. There is no other input required from the subject.

If convergence was achieved, in step 318, steps 314 and 316 are repeated, with the speed of the movement of panels 124 being increased to confirm convergence and to record the reaction time of both eyes. In step 320, the speed of movement of panels 128 is increased until convergence is lost at a recorded rate of speed and a perceived target distance. Throughout steps 314-320, the speed and the distance are recorded to determine the reaction time of the subject. Steps 304-320 can be repeated and an average can be calculated for the recorded values for that subject during a single evaluation period (i.e., an evaluation date).

The movement of panels 128 allows for headpiece 100 to rapidly present a target at one position and rapidly present the target in a different position (distance) while measuring the rate of re-convergence between the subject's eyes.

Figure 15:
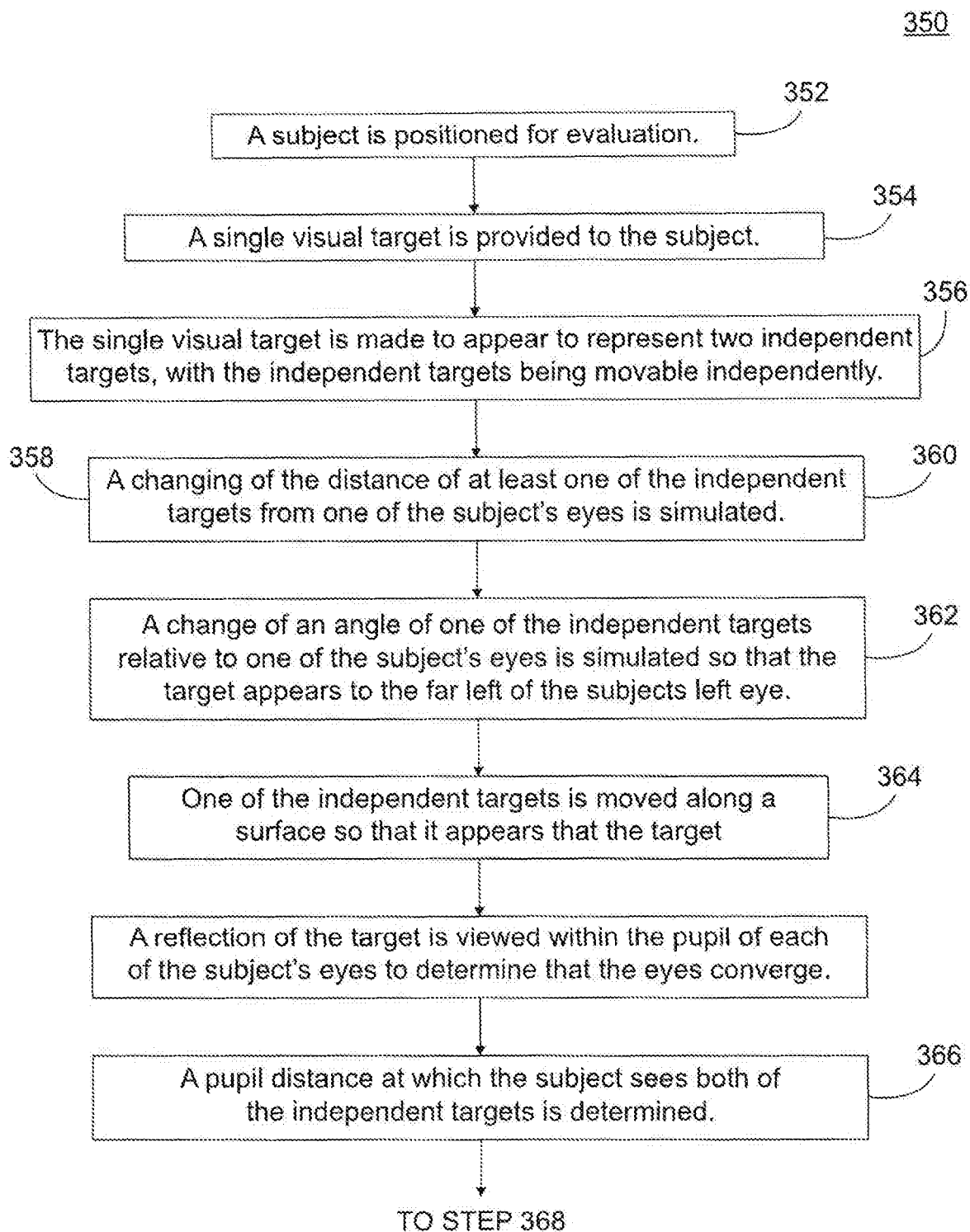
FIGS. 15 and 16 are a flowchart showing another exemplary method of using the device of the present invention.
Figure 16:
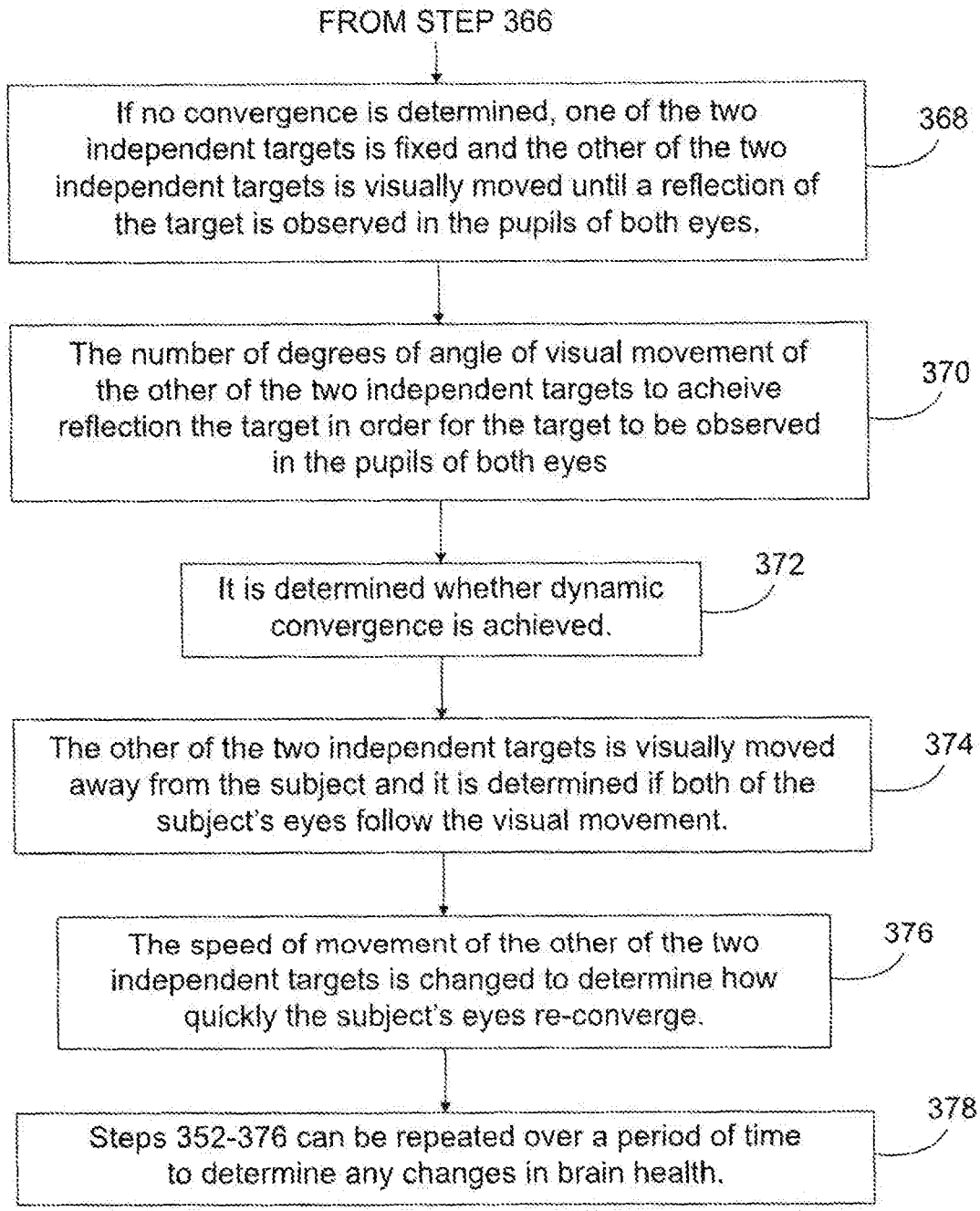

An exemplary method of determining the neurological condition in a subject will now be described with reference to flowchart 350 in FIGS. 15 and 16. The determination can be determining the convergence ability of the subject's brain.

In step 352, a subject is positioned for evaluation, which can include placing headpiece 100 over the subject's head and adjusting headband 102 so that headpiece is snugly retained on the subject's head. Camera 134 is locked onto both eyes. The distance from the eyes to camera 134 is fixed. Light source 120 is unobservable to subject to illuminate the subject's eyes. For this test, panels 128 include a reflective surface on a proximal side of each panel 128. In step 354, a single visual target is provided to the subject. In step 356, the single visual target is made to appear to represent two independent targets, with the independent targets being movable independently.

Figure 17:
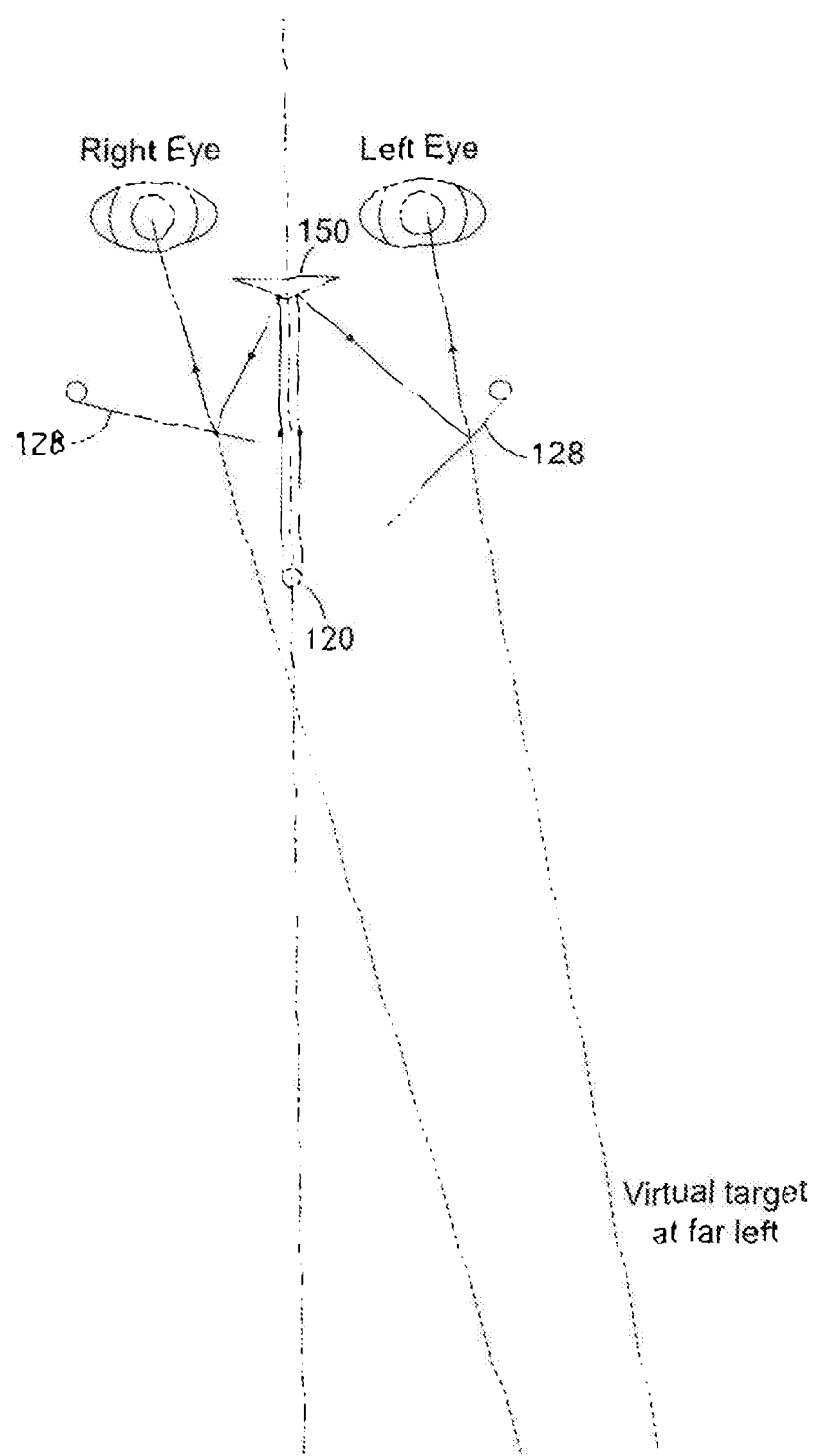
FIG. 17 is a schematic view showing a virtual target to the left of a left eye of a subject.
Figure 18:
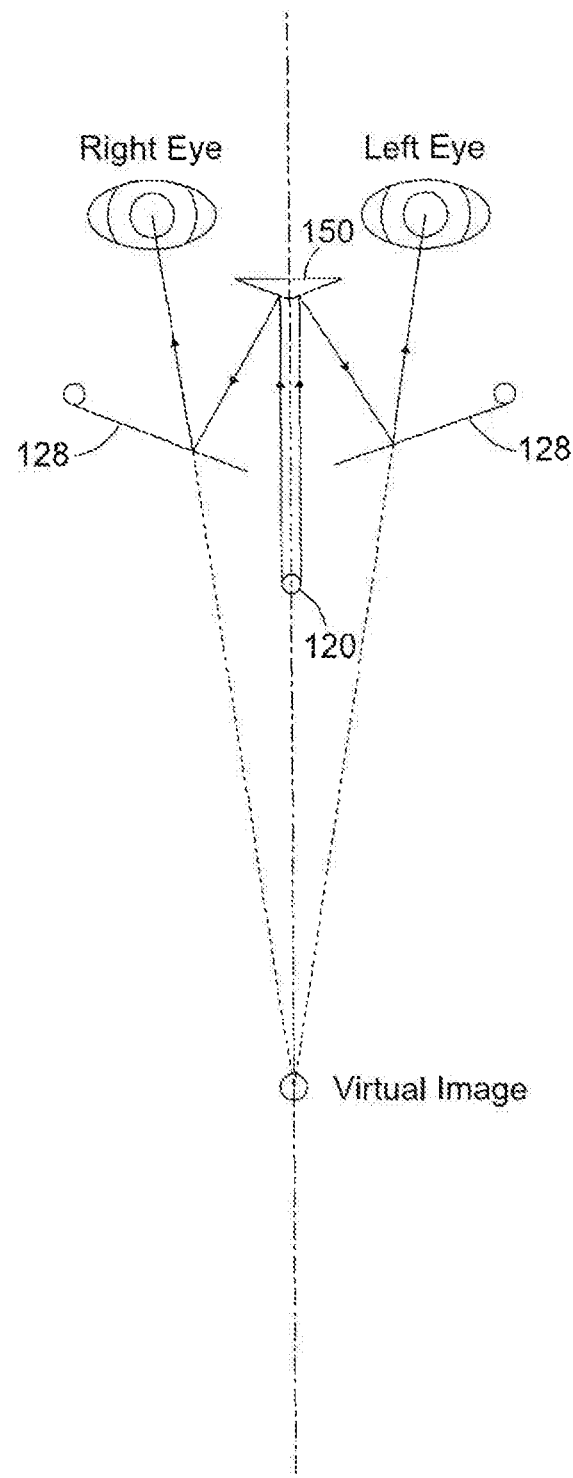
FIG. 18 is a schematic view showing the virtual target of FIG. 17 having been virtually moved.

In step 358, a changing of the distance of at least one of the independent targets from one of the subject's eyes is simulated and, in step 360, a change of an angle of one of the independent targets relative to one of the subject's eyes is simulated so that the target appears to the far left of the subject's left eye, as shown in FIG. 17. In step 362, one of the independent targets is moved along a surface so that it appears that the target moves to the location shown in FIG. 18. Typically, the target that is moved is the target associated with the non-converging eye. The movement comprises visually moving the one of the independent targets in a smooth continuous form.

In step 364, a reflection of the target is viewed within the pupil of each of the subject's eyes to determine that the eyes converge and, in step 366, a pupil distance at which the subject sees both of the independent targets is determined. In step 368, if no convergence is determined, one of the two independent targets is fixed and the other of the two independent targets is visually moved until a reflection the target is observed in the pupils of both eyes.

In step 370, the number of degrees of angle of visual movement of the other of the two independent targets to achieve reflection the target in order for the target to be observed in the pupils of both eyes is determined and in step 372, it is determined whether dynamic convergence is achieved.

In step 374, the other of the two independent targets is visually moved away from the subject and it is determined if both of the subject's eyes follow the visual movement. In step 376, the speed of movement of the other of the two independent targets is changed to determine how quickly the subject's eyes re-converge. In step 378, steps 352-376 can be repeated over a period of time to determine any changes in brain health.

Figure 19:
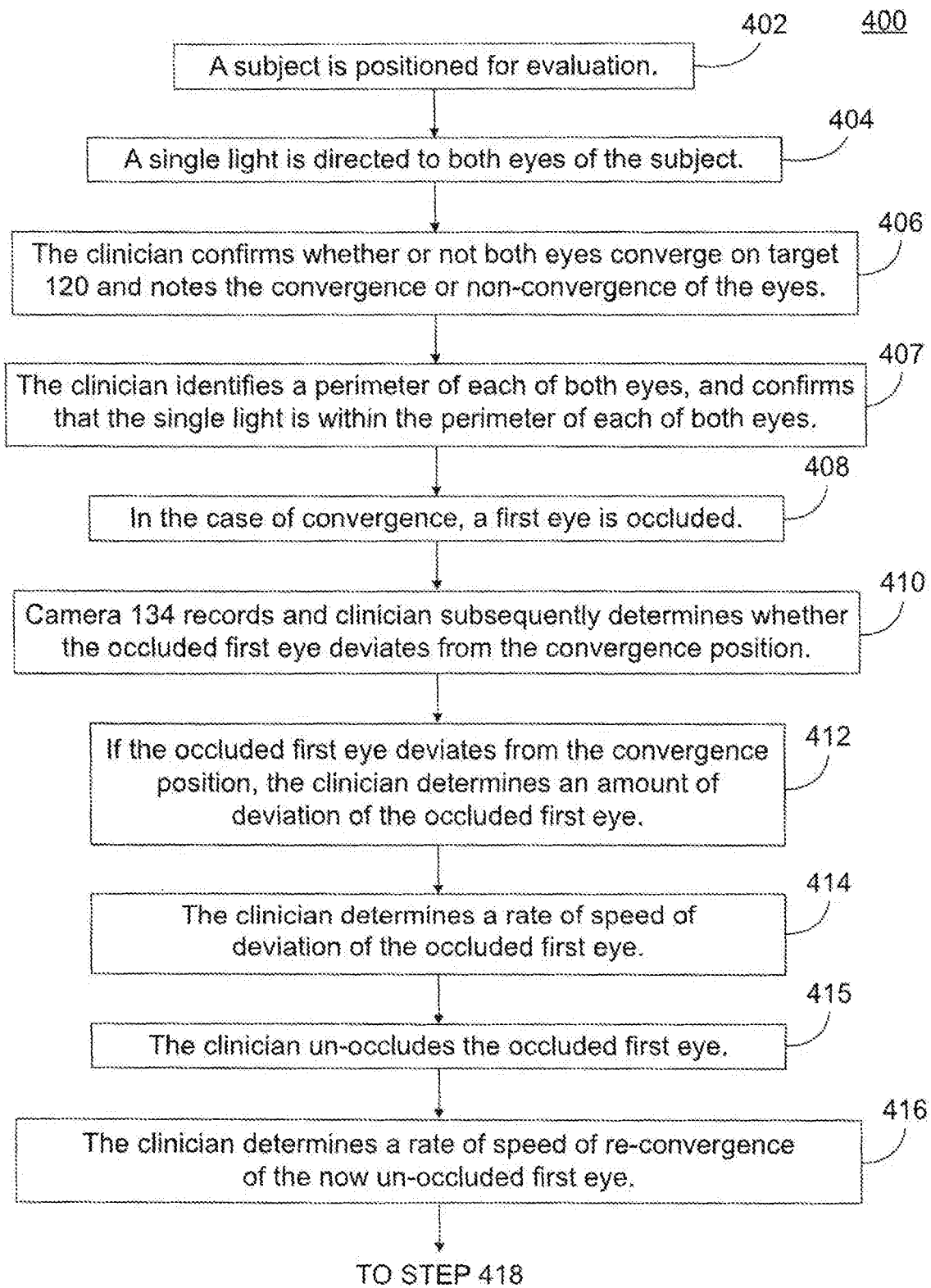
FIGS. 19-21 are a flowchart showing an alternative exemplary method of using the device of the present invention.
Figure 20:
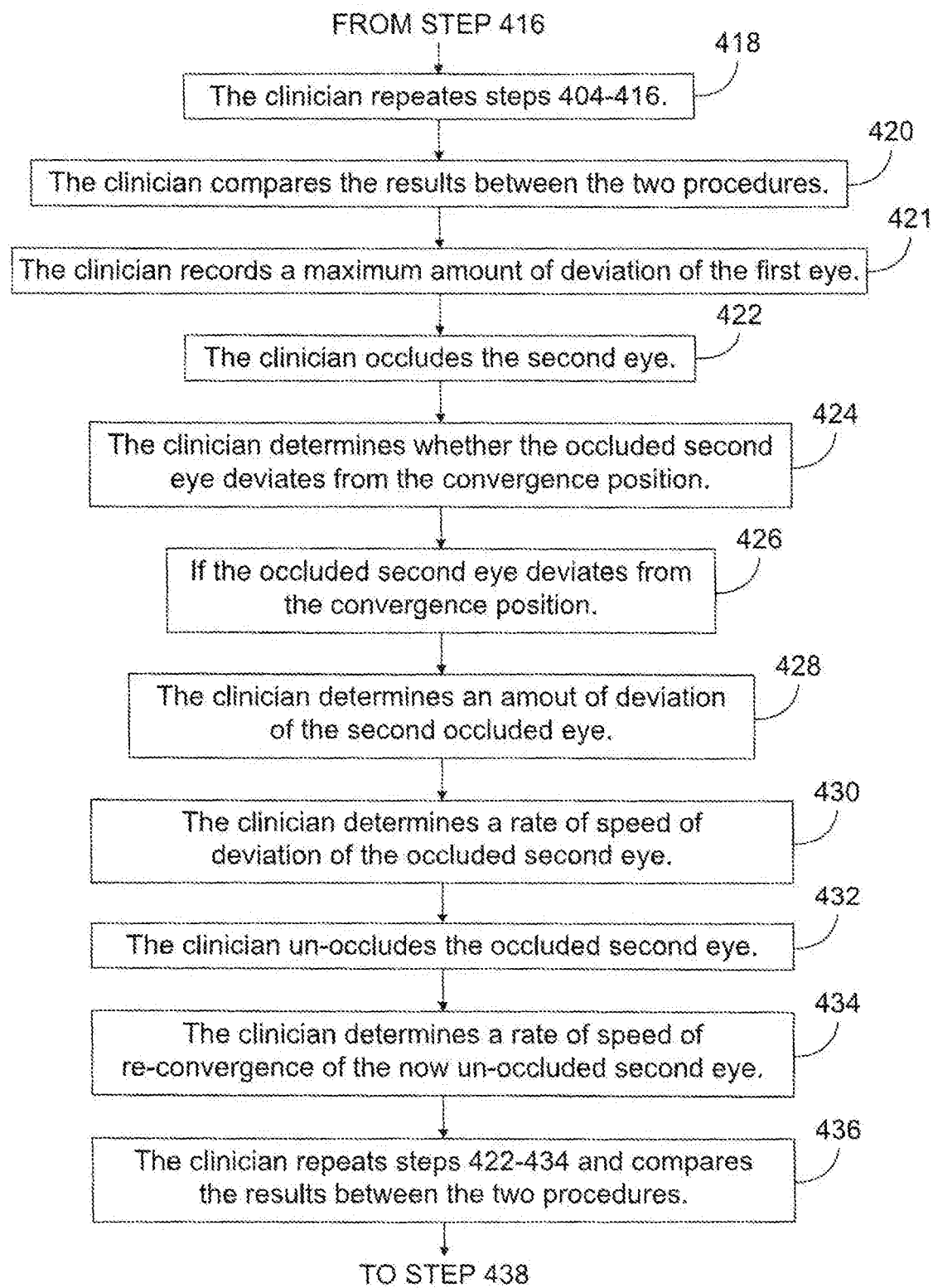
Figure 21:
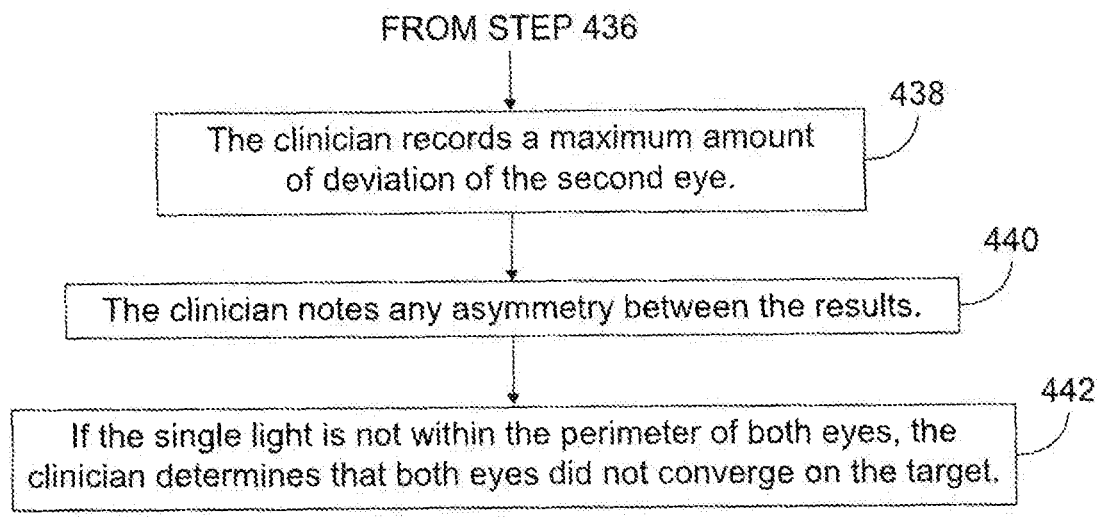

An exemplary method of determining the neurological condition in a subject will now be described with reference to flowchart 400 in FIGS. 19-21. In step 402, a subject is positioned for evaluation, which can include placing headpiece 100 over the subject's head and adjusting headband 102 so that headpiece is snugly retained on the subject's head.

In step 404, a single light is directed to both eyes of the subject. In an exemplary embodiment, the single light can be light source 120. Light source 120 can be used as a target for the subject to view with both eyes. A separate light source 251 is used to illuminate both eyes so that camera 134 can record the motion of the eyes during the procedure.

In step 406, the clinician or device control software confirms whether or not both eyes converge on target 120 and notes the convergence or non-convergence of the eyes. In step 407, the clinician or device control software identifies a perimeter of each of both eyes, and confirms that the single light is within the perimeter of each of both eyes.

Figure 22:
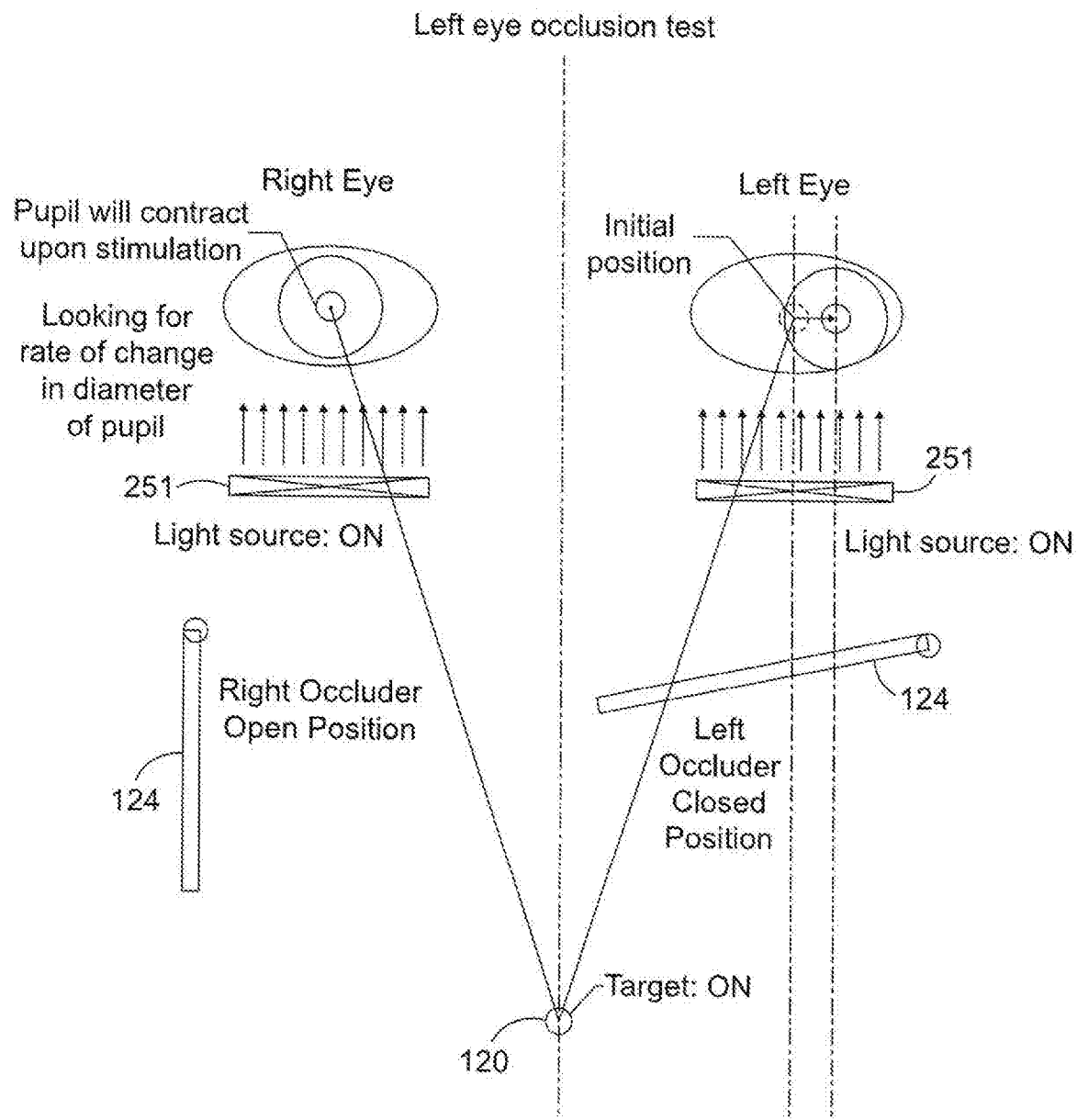
FIG. 22 is a schematic view of a left eye occlusion test showing deviation of the left eye after occlusion.

In the case of convergence, in step 408, a first eye is occluded and, in step 410, camera 134 records and clinician or device control software subsequently determines whether the occluded first eye deviates from the convergence position. FIG. 22 shows deviation of the left eye as a result of occlusion of that eye.

In step 412, if the occluded first eye deviates from the convergence position, the clinician or device control software determines an amount of deviation of the occluded first eye; and in step 414, the clinician or device control software determines a rate of speed of deviation of the occluded first eye. Next, in step 414, the clinician or device control software un-occludes the occluded first eye and, in step 415, the clinician or device control software determines a rate of speed of re-convergence of the now un-occluded first eye.

In step 418, the clinician or device control software repeats steps 404-416 and, in step 420, the clinician or device control software compares the results between the two procedures. In step 421, the clinician or device control software records a maximum amount of deviation of the first eye.

The clinician or device control software repeats the process for the second eye, namely, in step 422, the clinician or device control software occludes the second eye, and, in step 424, determines whether the occluded second eye deviates from the convergence position. In step 426, if the occluded second eye deviates from the convergence position, then, in step 428, the clinician or device control software determines an amount of deviation of the occluded second eye and in step 430, determines a rate of speed of deviation of the occluded second eye.

Next, in step 432, the clinician or device control software un-occludes the occluded second eye and, in step 434, determines a rate of speed of re-convergence of the now un-occluded second eye. In step 436, the clinician or device control software repeats steps 422-434 and compares the results between the two procedures. In step 438, the clinician or device control software records a maximum amount of deviation of the second eye and, in step 440, notes any asymmetry between the results.

If the single light is not within the perimeter of both eyes, the clinician or device control software determines that both eyes did not converge on the target. If, in step 406, the eyes do not converge, then, in step 442, the clinician or device control software records the non-convergence.

Figure 23:
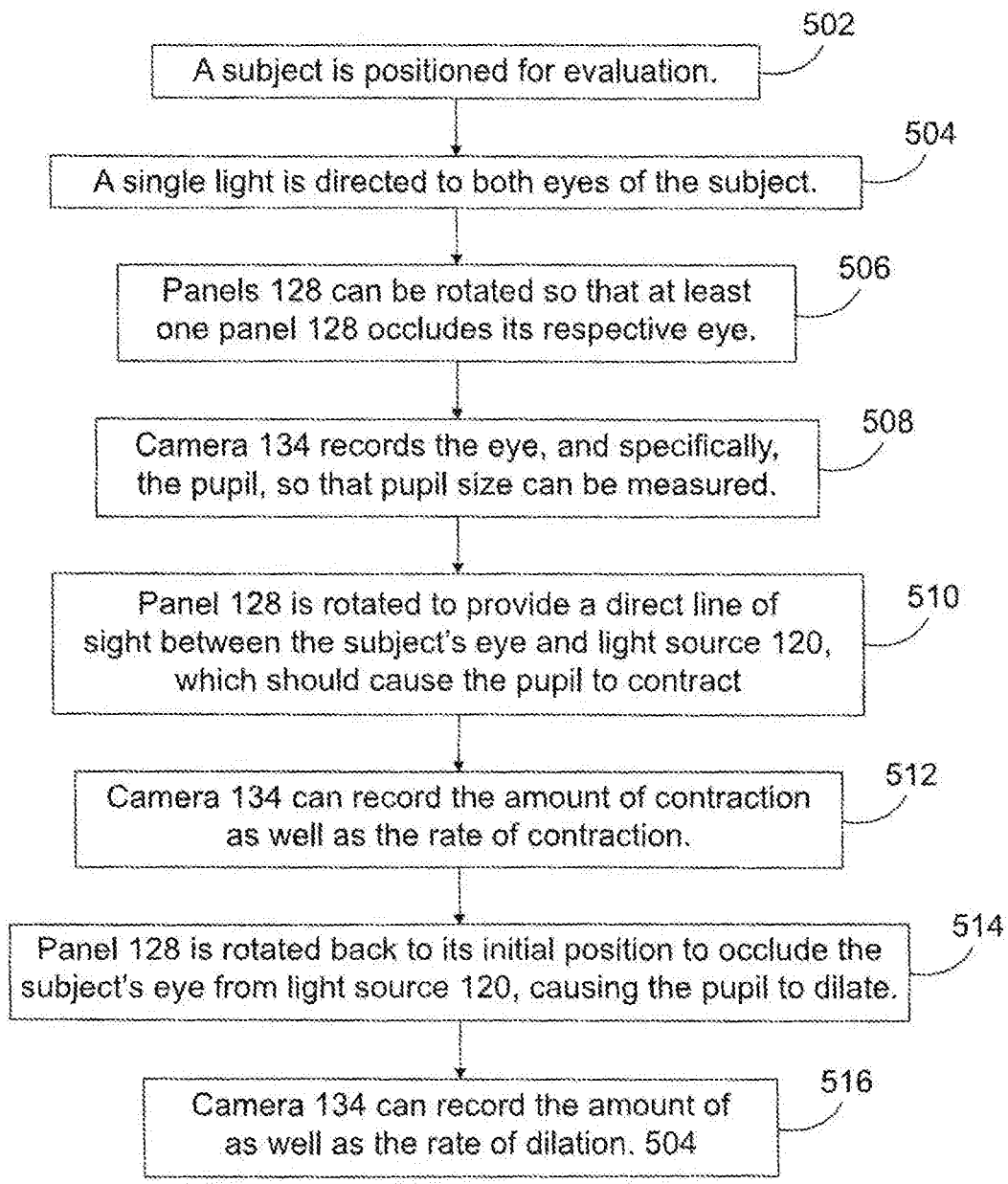
FIG. 23 is a flowchart showing another alternative exemplary method of using the device of the present invention.

Additionally, referring to flowchart 500 shown in FIG. 23, headpiece 100 can be used to measure the amount and rate of pupil dilation to determine potential brain performance deficiency.

In step 502, a subject is positioned for evaluation, which can include placing headpiece 100 over the subject's head and adjusting headband 102 so that headpiece is snugly retained on the subject's head.

Figure 24:
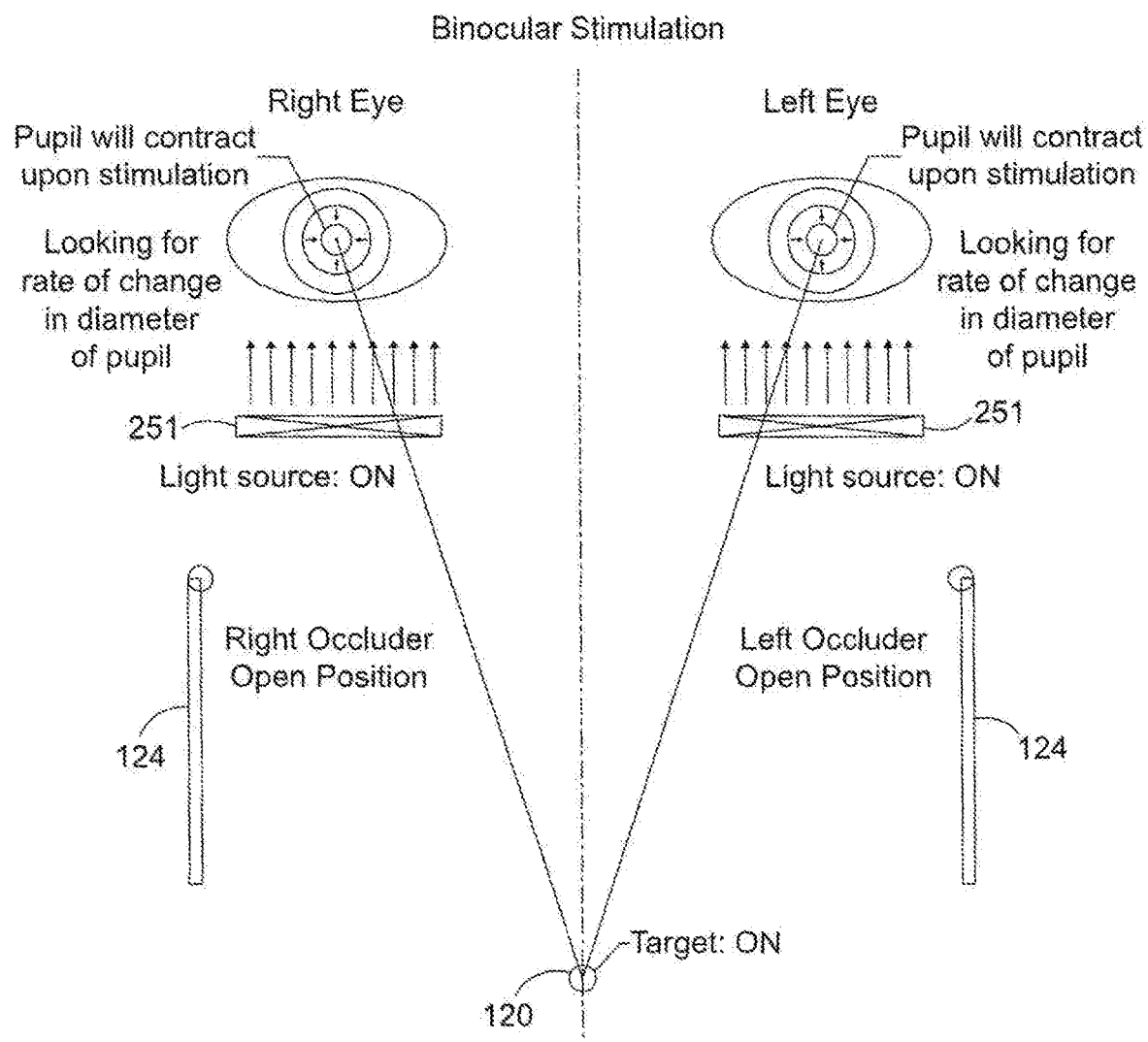
FIG. 24 is a schematic view of binocular stimulation to measure and record the amount and rate of size change of a subject's pupils based on occlusion or non-occlusion of the pupils.

In step 504, a single light is directed to both eyes of the subject as shown in FIG. 24. In an exemplary embodiment, the single light can be light source 120. Light source 120 can be used as a target for the subject to view with both eyes. The target is occluded to one eye, blocking the eye from seeing the target. Light 251 at the occluded eye is cycled on and off, illuminating the occluded eye. Camera 134 then records the dilation or contraction size and rate of the occluded eye.

Figure 25:
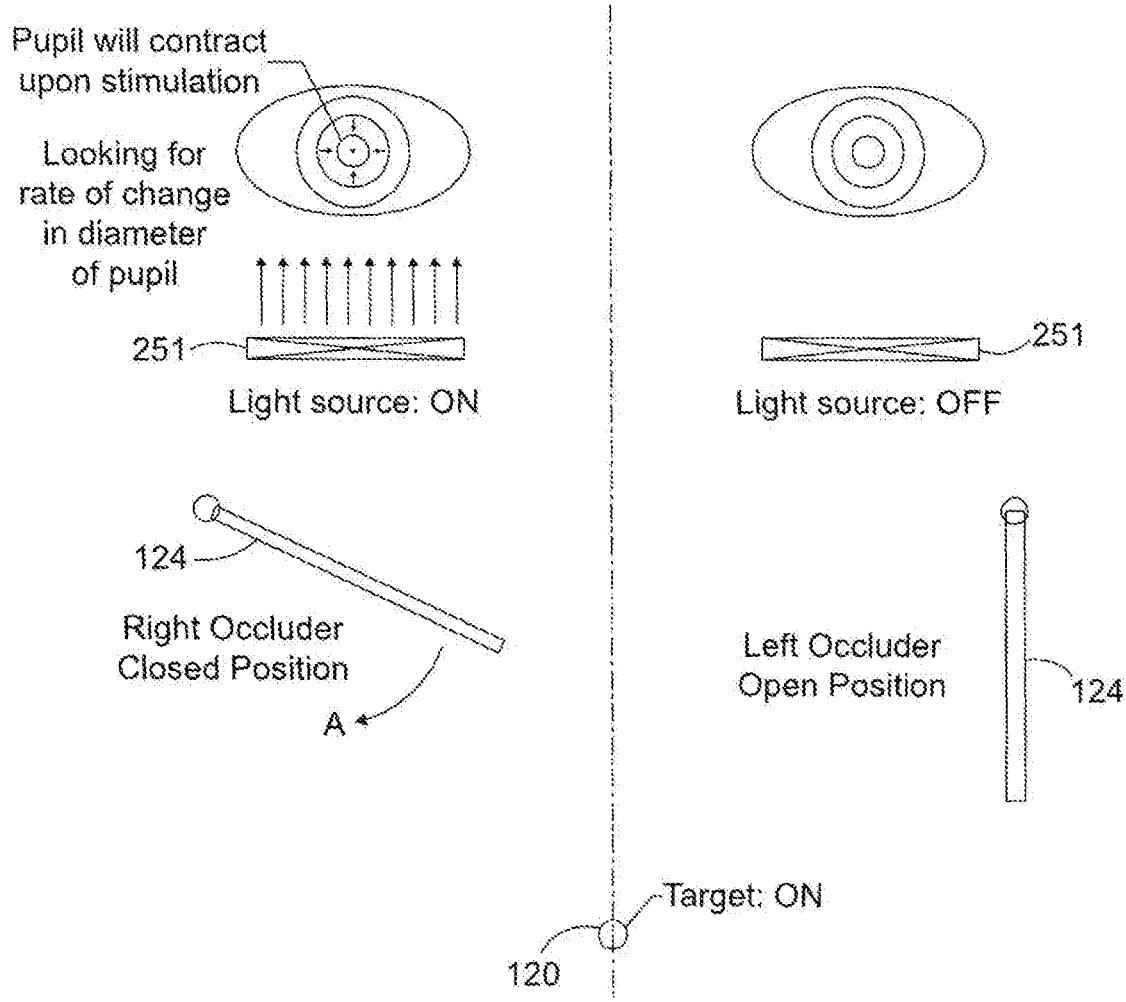
FIG. 25 is a schematic view of an evaluation to determine the amount and rate of pupil contraction using the headpiece shown in FIGS. 1 and 2.

In step 506, panels 128 can be rotated so that at least one panel 128 occludes its respective eye. Light 251 at the occluded eye is cycled on and off, illuminating/de-luminating the occluded eye. In step 508, camera 134 records the eye, and specifically, the pupil, so that pupil size can be measured. In step 510, panel 128 is rotated in the direction of arrow "A", shown in FIG. 25, to provide a direct line of sight between the subject's eye and light source 120. Light 251 at the un-occluded eye is cycled on, illuminating the un-occluded eye, which should cause the pupil to contract. In step 512, camera 134 can record the amount of contraction (such as in millimeters) as well as the rate of contraction.

Figure 26:
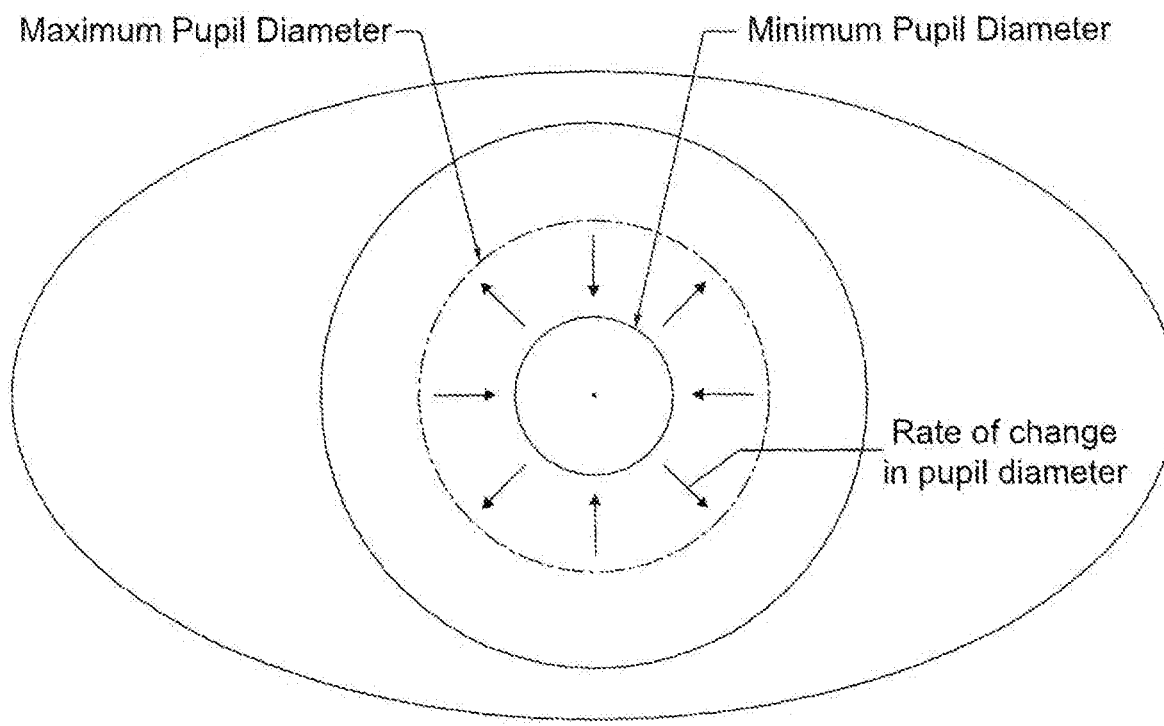
FIG. 26 is an enlarged view of a pupil of a subject showing maximum and minimum pupil sizes during the evaluation associated with FIG. 25.

The amount and rate of dilation of the pupil can also be measured. In step 514, panel 128 is rotated back to its initial position to occlude the subject's eye from light source 120, causing the pupil to dilate. In step 516, camera 134 can record the amount of dilation (such as in millimeters) as well as the rate of dilation. FIG. 26 shows maximum and minimum pupil sizes that can be measured during steps 508-516.

Headpiece 100 is configured so that the above described procedure is performed without asking the subject if both eyes converged on the target, enabling the methods described above to be performed without causing unwanted movement of both eyes.

It will be further understood that various changes in the details, materials, and arrangements of the parts which have been described and illustrated in order to explain the nature of this invention may be made by those skilled in the art without departing from the scope of the invention as expressed in the following claims.

I claim:

1. A method for determining a neurological condition in a subject, the method comprising the steps of:
    (a) electronically recording the pupils in the eyes of the subject and determining perimeters of the pupils;
    (b) presenting a single physical target to the subject;
    (c) electronically recording the pupils of the subject to determine whether an image of the target appears within the perimeter of the pupils of both eyes simultaneously;
    (d) determining whether convergence occurs when the image of the target appears in both eyes simultaneously, or whether lack of convergence occurs when the image of the target does not occur simultaneously, resulting in a non-converging eye; and
    (e) electronically recording the results of whether or not convergence occurs.

2. The method according to claim 1, wherein step (b) comprises the single physical target being a light source.

3. The method according to claim 1, further comprising, if lack of convergence occurs, the step of:
    (f) operating a device to simulate apparent movement of the target until convergence occurs.

4. A method for determining a neurological condition in a subject, the method comprising the steps of:
    (a) electronically recording the pupils in the eyes of the subject and determining perimeters of the pupils;
    (b) presenting a single physical target to the subject;
    (c) electronically recording the pupils of the subject to determine whether an image of the target appears within the perimeter of the pupils of both eyes simultaneously;
    (d) determining whether convergence occurs when the image of the target appear in both eye simultaneously, or whether lack of convergence occurs when the image of the target does not occur simultaneously, resulting in a non-converging eye; and
    (e) electronically recording the results of whether or not convergence occurs;
    (f) operating a device to simulate apparent movement of the target until convergence occurs and
    (g) recording the amount that the device was operated.

5. The method according to claim 4, further comprising the step of:
    (h) recording an apparent distance from the target to the non-converging eye.

6. The method according to claim 5, further comprising the step of:
    (i) moving the apparent image of the target to an infinite distance from the subject's eyes.

7. The method according to claim 6, further comprising the step of
    (j) using a camera to track movement of each eye while the apparent image of the target is moving to the infinite distance.

8. The method according to claim 7, further comprising the step of:
    (k) moving the apparent image of the target from the infinite distance to a predetermined distance from the subject's eyes.

9. The method according to claim 8, further comprising the step of:
    (l) determining whether convergence was maintained during step (k).

10. The method according to claim 9, further comprising, if convergence was maintained, the step of:
    (m) repeating steps (i)-(l) while increasing a speed of the operation of the device.

11. The method according to claim 10, further comprising the step of:
    (n) repeating step (m) until convergence is lost.

12. The method according to claim 11, further comprising the step of:
    (o) recording the speed of the operation of the device and a perceived distance of the target from the subject's eyes when convergence was lost.

\* \* \* \* \*